(12) United States Patent
Sanghvi et al.

(10) Patent No.: US 8,222,201 B2
(45) Date of Patent: Jul. 17, 2012

(54) CRYSTALLINE FORM OF LINACLOTIDE

(76) Inventors: Ritesh Sanghvi, Commack, NY (US);
Andreas Grill, Hauppauge, NY (US);
Rahul Surana, Coram, NY (US);
Haijian Zhu, Smithtown, NY (US)

( * ) Notice: Subject to any disclaimer, the term of this patent is extended or adjusted under 35 U.S.C. 154(b) by 352 days.

(21) Appl. No.: 12/621,272

(22) Filed: Nov. 18, 2009

(65) Prior Publication Data

US 2010/0125056 A1    May 20, 2010

Related U.S. Application Data

(60) Provisional application No. 61/116,156, filed on Nov. 19, 2008.

(51) Int. Cl.
| | | |
|---|---|---|
| *A61K 38/00* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |

(52) U.S. Cl. .................................... 514/1.1; 530/327

(58) Field of Classification Search ................... None
See application file for complete search history.

(56) References Cited

U.S. PATENT DOCUMENTS

| | | |
|---|---|---|
| 7,304,036 B2 | 12/2007 | Currie et al. |
| 7,371,727 B2 | 5/2008 | Currie et al. |
| 2006/0258593 A1 | 11/2006 | Currie et al. |
| 2006/0281682 A1 | 12/2006 | Currie et al. |
| 2007/0010450 A1 | 1/2007 | Currie et al. |
| 2007/0010543 A1 | 1/2007 | Ashburn |
| 2008/0227685 A1 | 9/2008 | Currie et al. |
| 2009/0005534 A1 | 1/2009 | Currie et al. |
| 2009/0062207 A1 | 3/2009 | Currie et al. |

FOREIGN PATENT DOCUMENTS

WO    WO/2008/137318    11/2008

OTHER PUBLICATIONS

International Search Report and Written Opinion of International Searching Authority for PCT/US09/65001 (International counterpart to U.S. Appl. No. 12/621,272) mailed Feb. 7, 2010.
Andresen et al., Linaclotide Acetate, Drugs of the Future 33(7), 570-576 (Jul. 2008).

*Primary Examiner* — Marcela M Cordero Garcia

(57) ABSTRACT

The present invention relates to crystalline forms of linaclotide, as well as to various methods and processes for the preparation and use of the crystalline forms.

6 Claims, 13 Drawing Sheets

CRYSTALLINE FORM OF LINACLOTIDE

This application claims the benefit of U.S. Provisional Application No. 61/116,156, filed Nov. 19, 2008, the entire contents of which are hereby incorporated by reference.

FIELD OF THE INVENTION

The present invention relates to a novel α-crystalline form of linaclotide, as well as processes for the preparation of the α-crystalline form, compositions comprising the α-crystalline form, and methods of using the α-crystalline form.

SEQUENCE LISTING

This application incorporates by reference the Sequence Listing entitled lin_ST25.txt (529 bytes) created on Dec. 18, 2009 and filed with the U.S. Patent and Trademark Office on Dec. 28, 2009, as well as the Sequence Listing entitled lin and hydrolysis product.txt (529 bytes) created on Apr. 13, 2012 and filed with the U.S. Patent and Trademark Office on Apr. 13, 2012.

BACKGROUND OF THE INVENTION

U.S. Pat. No. 7,304,036 discloses peptides that act as agonists of the guanylate cyclase C (GC-C) receptor for the treatment of gastrointestinal disorders. One particular peptide disclosed therein is linaclotide, which consists of the following amino acid sequence: Cys Cys Glu Tyr Cys Cys Asn Pro Ala Cys Thr Gly Cys Tyr (SEQ ID NO 1).

U.S. Pat. Nos. 7,304,036 and 7,371,727 disclose methods for the preparation of linaclotide and related peptides. The contents of U.S. Pat. Nos. 7,304,036 and 7,371,727 are incorporated herein by reference, in their entirety.

There remains a need in the art for improved forms of linaclotide having improved properties.

The present invention relates to a new crystalline form or polymorph of linaclotide, which has surprisingly and unexpectedly enhanced properties, such as enhanced or greater stability, as compared to amorphous linaclotide. In addition, such a crystalline form of linaclotide may have enhanced storage stability and enhanced stability against chemical degradation as compared to amorphous linaclotide.

SUMMARY OF THE INVENTION

The present invention relates to a novel α-crystalline form of linaclotide. Various methods and processes for the preparation and use of the crystalline form are also described herein.

DETAILED DESCRIPTION OF THE INVENTION

Figure 1:
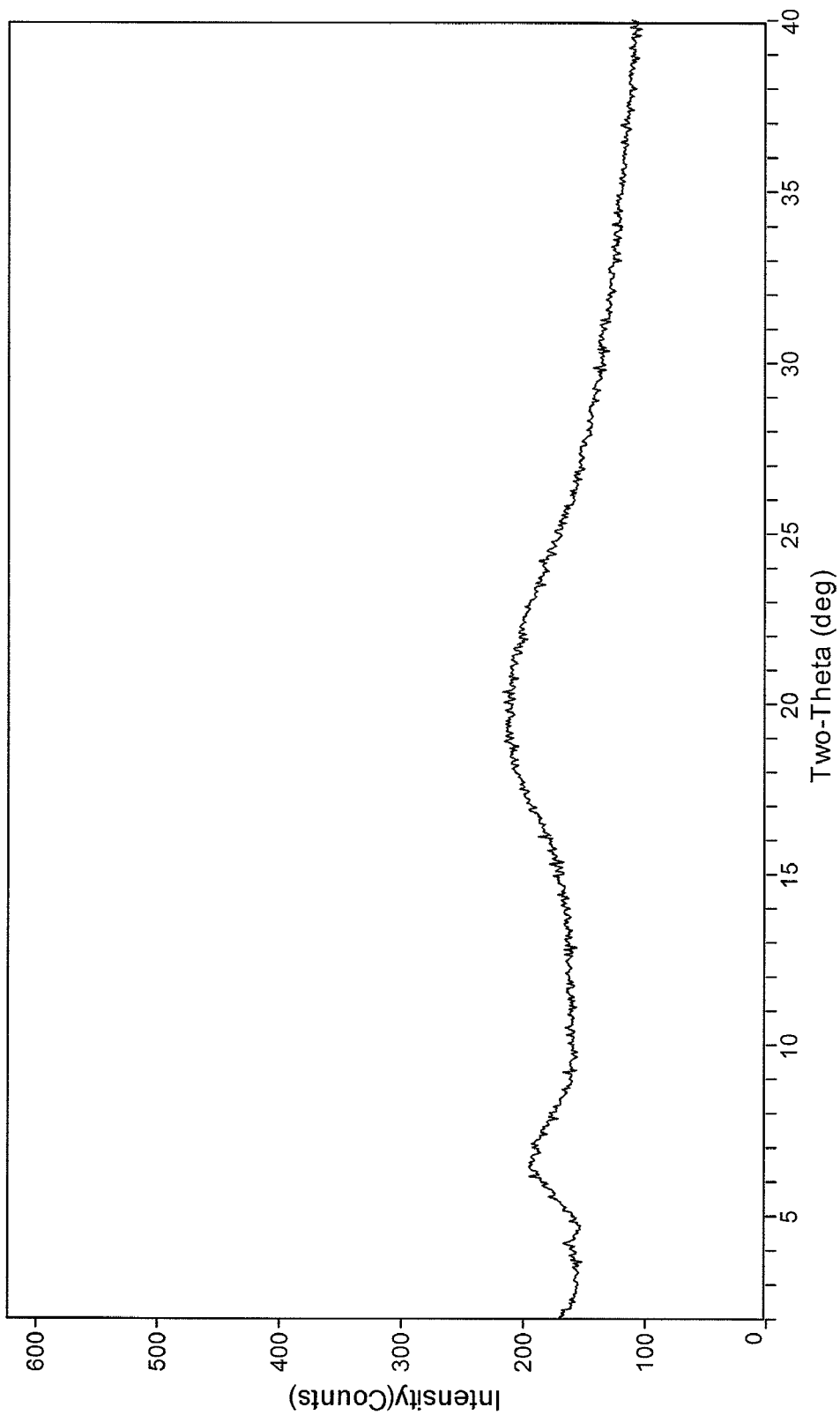
FIG. 1 shows the X-ray powder diffraction pattern of amorphous linaclotide.

The present invention provides crystalline forms of linaclotide. The methods for preparation as disclosed in U.S. Pat. Nos. 7,304,036 and 7,371,727 yield linaclotide in an amorphous state. The X-ray powder diffraction pattern of amorphous linaclotide is illustrated in FIG. 1.

In one aspect, the present invention relates to crystalline forms of linaclotide, specifically α-crystalline forms of linaclotide (α form linaclotide).

In some embodiments, the α form linaclotide is characterized by an X-ray powder diffraction pattern comprising a peak at about 6.2+/−0.5 degrees 2θ.

In some embodiments, the α form linaclotide is characterized by an X-ray powder diffraction pattern comprising a peak at about 7.8+/−0.5 degrees 2θ.

In some embodiments, the α form linaclotide is characterized by an X-ray powder diffraction pattern comprising a peak at about 8.6+/−0.5 degrees 2θ.

In certain embodiments, the α form linaclotide is characterized by an X-ray powder diffraction pattern comprising a peak at about 9.7+/−0.5 degrees 2θ.

In certain embodiments, the α form linaclotide is characterized by an X-ray powder diffraction pattern comprising a peak at about 10.3+/−0.5 degrees 2θ.

In certain embodiments, the α form linaclotide is characterized by an X-ray powder diffraction pattern comprising a peak at about 11.4+/−0.5 degrees 2θ.

In certain embodiments, the α form linaclotide is characterized by an X-ray powder diffraction pattern comprising a peak at about 14.3+/−0.5 degrees 2θ.

In certain embodiments, the α form linaclotide is characterized by an X-ray powder diffraction pattern comprising a peak at about 16.0+/−0.5 degrees 2θ.

In certain embodiments, the α form linaclotide is characterized by an X-ray powder diffraction pattern comprising a peak at about 17.9+/−0.5 degrees 2θ.

In certain embodiments, the α form linaclotide is characterized by an X-ray powder diffraction pattern comprising a peak at about 19.5+/−0.5 degrees 2θ.

In certain embodiments, the α form linaclotide is characterized by an X-ray powder diffraction pattern comprising a peak at about 20.9+/−0.5 degrees 2θ.

In certain embodiments, the α form linaclotide is characterized by an X-ray powder diffraction pattern comprising a peak at about 21.6+/−0.5 degrees 2θ.

In certain embodiments, the α form linaclotide is characterized by an X-ray powder diffraction pattern comprising a peak at about 22.6+/−0.5 degrees 2θ.

In certain embodiments, the α form linaclotide is characterized by an X-ray powder diffraction pattern comprising a peak at about 23.9+/−0.5 degrees 2θ.

In certain embodiments, the α form linaclotide is characterized by an X-ray powder diffraction pattern comprising a peak at about 24.4+/−0.5 degrees 2θ.

In certain embodiments, the α form linaclotide is characterized by an X-ray powder diffraction pattern comprising a peak at about 25.2+/−0.5 degrees 2θ.

In exemplary embodiments, the α form linaclotide is characterized by an X-ray powder diffraction pattern comprising peaks at about 6.2, about 7.8, about 11.4, about 16.0, about 19.5, and at about 23.9+/−0.5 degrees 2θ.

In exemplary embodiments, the α form linaclotide is characterized by an X-ray powder diffraction pattern comprising peaks at about 6.2, about 7.8, about 8.6, about 9.7, about 10.3, about 11.4, about 14.3, about 16.0, about 17.9, about 19.5, about 20.9, about 21.6, about 22.6, about 23.9, about 24.4, and at about 25.2+/−0.5 degrees 2θ.

In exemplary embodiments, the α form linaclotide is characterized by an X-ray powder diffraction pattern comprising peaks at about 6.2 and at about 7.8+/−0.5 degrees 2θ. In exemplary embodiments, the α form linaclotide is characterized by an X-ray powder diffraction pattern comprising peaks at about 7.8 and at about 23.9+/−0.5 degrees 2θ. In exemplary embodiments, the α form linaclotide is characterized by an X-ray powder diffraction pattern comprising peaks at about 6.2, about 7.8 and about 23.9+/−0.5 degrees 2θ.

In exemplary embodiments, the α form linaclotide is characterized by an X-ray powder diffraction pattern comprising peaks at about 6.2, about 7.8, about 19.5 and about 23.9+/−0.5 degrees 2θ. In exemplary embodiments, the α form linaclotide is characterized by an X-ray powder diffraction pattern comprising peaks at about 6.2, about 7.8, about 22.6 and about 23.9+/−0.5 degrees 2θ.

In exemplary embodiments, the α form linaclotide is characterized by an X-ray powder diffraction pattern comprising peaks at about 6.2, about 7.8, about 23.9+/−0.5 degrees 2θ and optionally one or more peaks at about 19.5+/−0.5 degrees 2θ and/or about 22.6+/−0.5 degrees 2θ.

In exemplary embodiments, the α form linaclotide is characterized by an X-ray powder diffraction pattern comprising peaks at about 6.2, about 7.8, about 19.5, about 22.6 and about 23.9+/−0.5 degrees 2θ.

Figure 2:
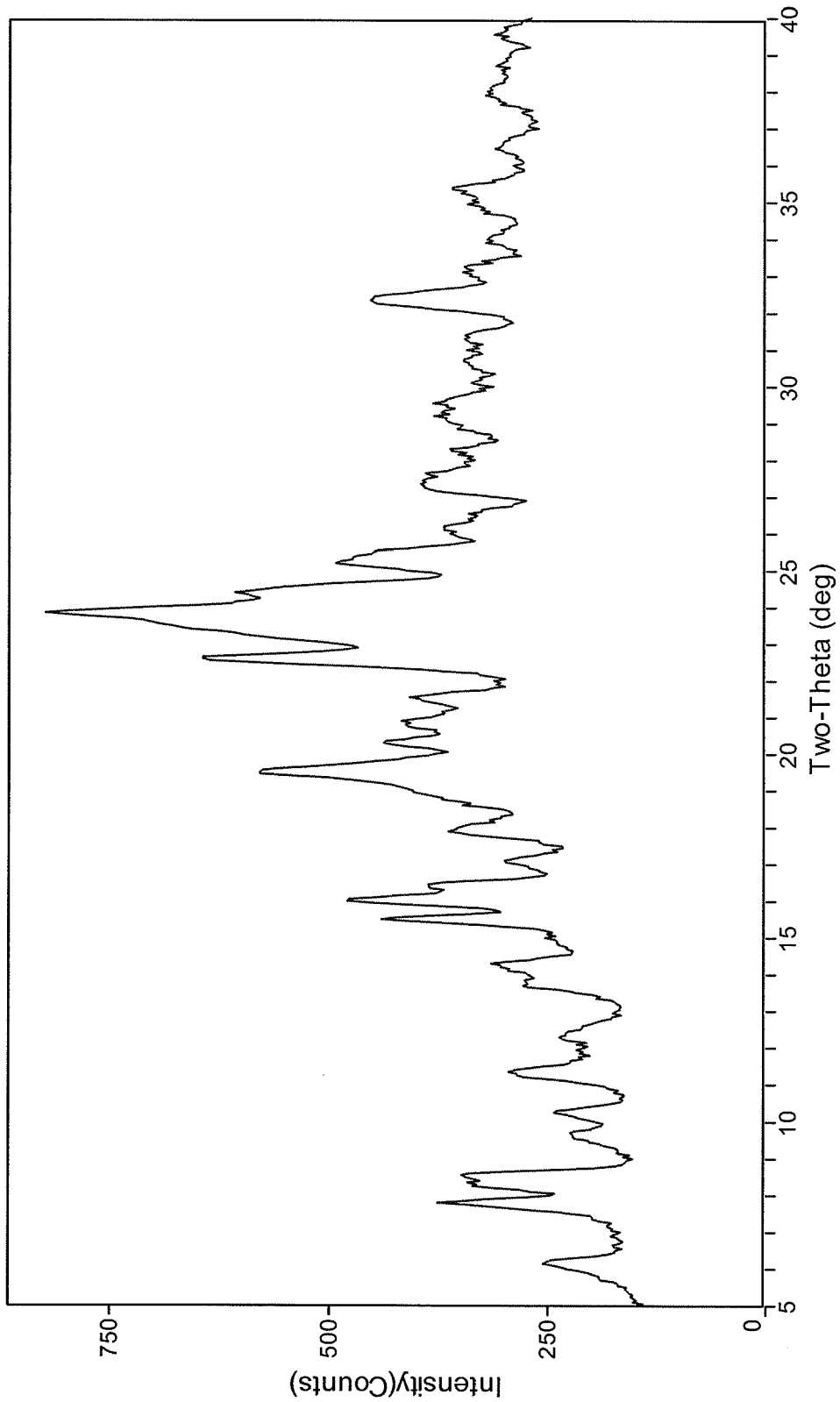
FIG. 2 shows the X-ray powder diffraction pattern of an α-crystalline form of linaclotide.
Figure 3:
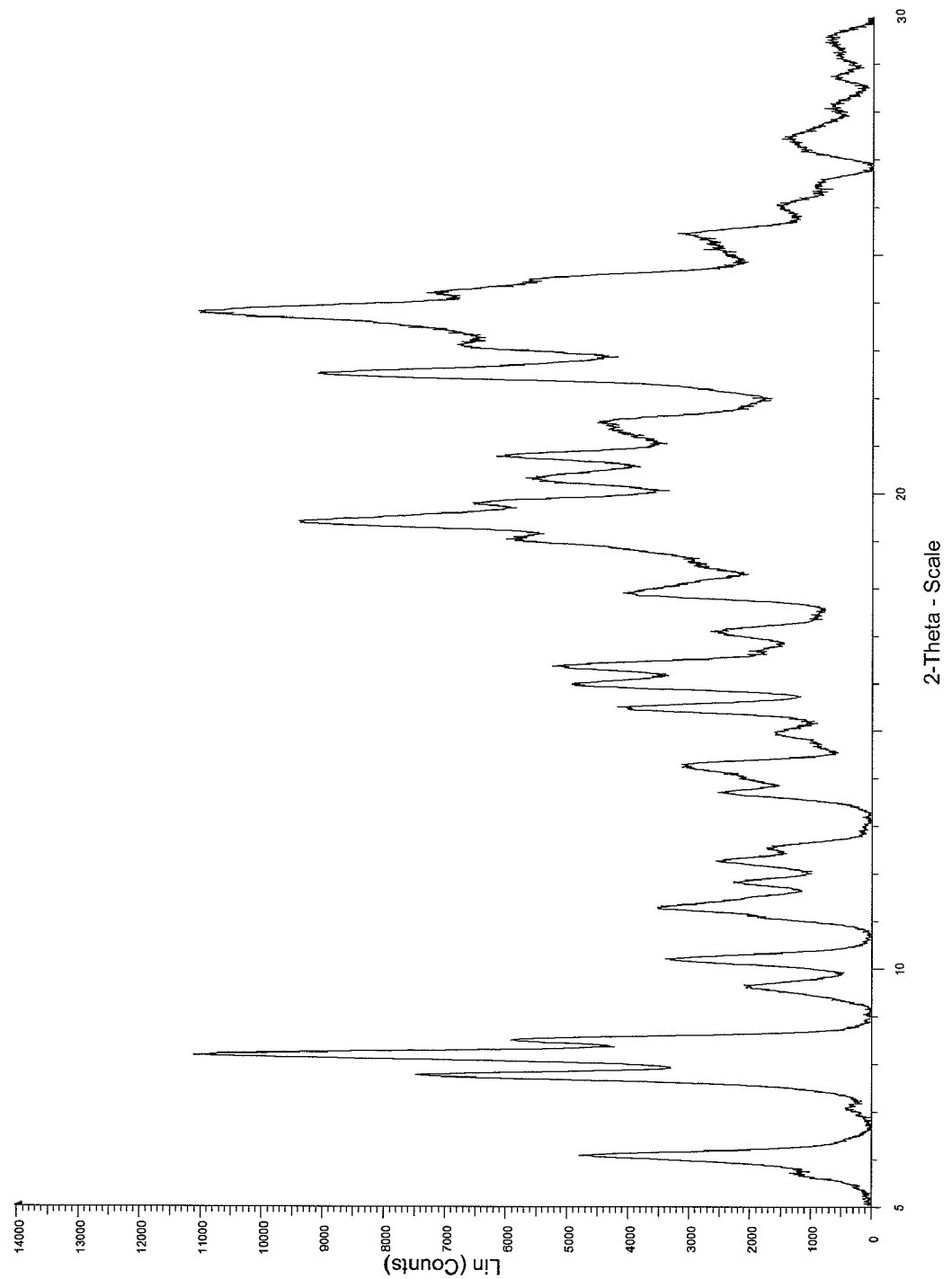
FIG. 3 shows the X-ray powder diffraction pattern of an α-crystalline form of linaclotide.

In exemplary embodiments, the α form linaclotide is characterized by an X-ray powder diffraction pattern substantially as shown in FIG. 2 or FIG. 3.

In some embodiments, the α form linaclotide is characterized by an X-ray powder diffraction pattern comprising one or more peaks as provided in Table 1. In some embodiments, the α form linaclotide is characterized by an X-ray powder diffraction pattern comprising one or more peaks at about 5.7, about 7.7, about 23.8+/−0.5 degrees 2θ and optionally one or more peaks at about 7.0, about 8.5, about 9.6, about 10.2, about 11.3, about 12.6, about 13.7, about 14.3, about 15.5, about 16.4, about 17.1, about 17.9, about 18.5, about 19.4, about 20.8, about 21.5, about 22.5, about 23.1, about 24.5, about 25.5, about 26.1, about 27.5, about 28.2, about 28.8 and/or about 29.6+/−0.5 degrees 2θ. As used herein, unless otherwise indicated, the phrase "one or more peaks" should be understood to be inclusive of (i) crystalline forms that have XRD peaks at every peak value recited after this phrase, (ii) crystalline forms that have an XRD peak at only one of the peak values recited after this phrase, as well (iii) crystalline forms that have XRD peaks at two or more (e.g., three or more, four or more, five or more, six or more, or even seven or more) of the peak values recited after this phrase.

In some embodiments, the α form linaclotide is characterized by an X-ray powder diffraction pattern comprising peaks at about 5.7 and about 7.7+/−0.5 degrees 2θ. In some embodiments, the α form linaclotide is characterized by an X-ray powder diffraction pattern comprising peaks at about 5.7, about 7.7 and about 23.8+/−0.5 degrees 2θ.

In some embodiments, the α form linaclotide is characterized by an X-ray powder diffraction pattern comprising peaks at about 5.7, about 7.7, about 23.8+/−0.5 degrees 2θ and optionally one or more peaks at about 19.4+/−0.5 degrees 2θ and/or at about 22.5+/−0.5 degrees 2θ.

In some embodiments, the α form linaclotide is characterized by an X-ray powder diffraction pattern comprising peaks at about 5.7, about 7.7, about 19.4 and about 23.8+/−0.5 degrees 2θ.

In some embodiments, the α form linaclotide is characterized by an X-ray powder diffraction pattern comprising peaks at about 5.7, about 7.7, about 22.5 and about 23.8+/−0.5 degrees 2θ. In some embodiments, the α form linaclotide is characterized by an X-ray powder diffraction pattern comprising peaks at about 5.7, about 7.7, about 19.4, about 22.5 and about 23.8+/−0.5 degrees 2θ.

Figure 6:
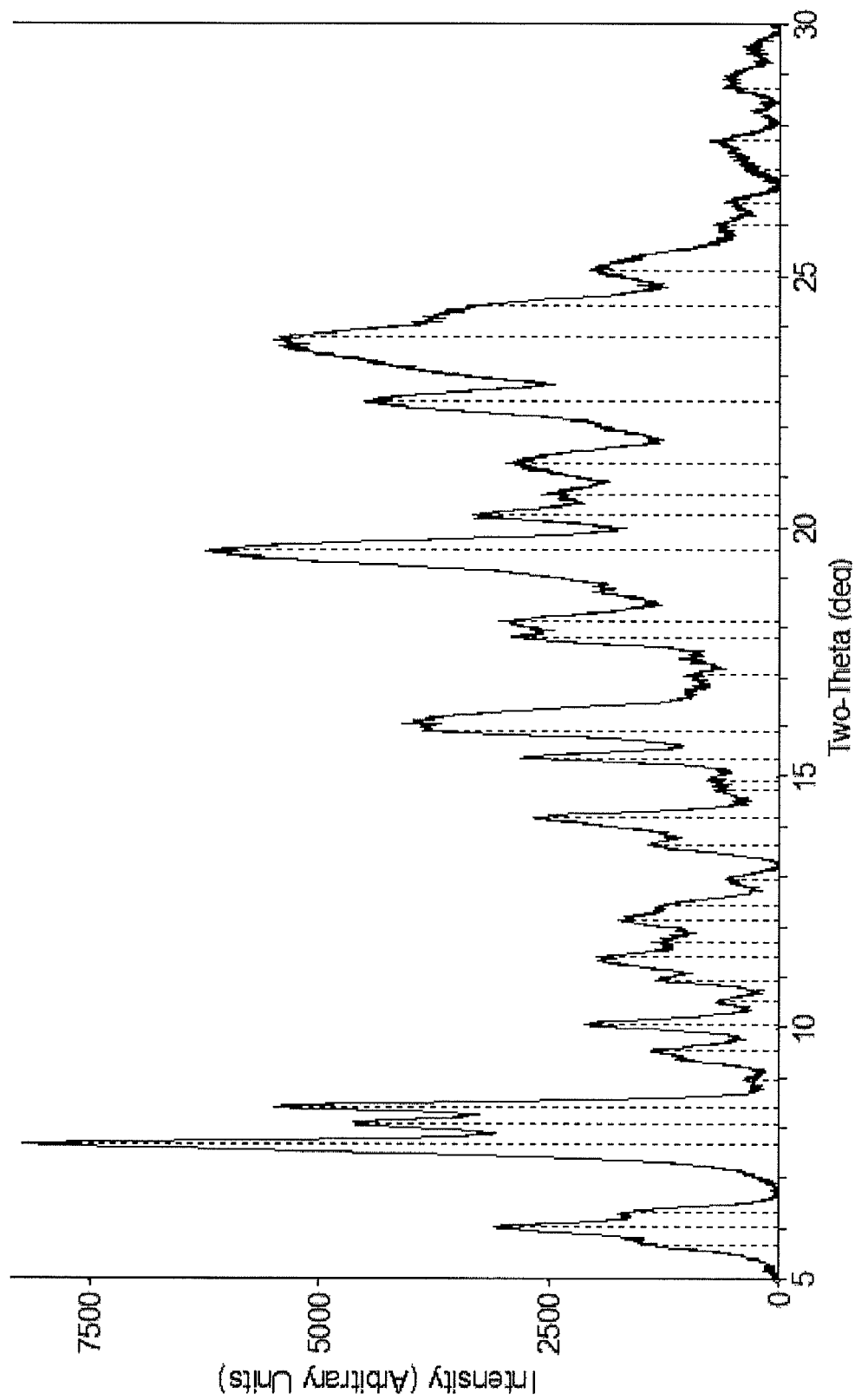
FIG. 6 shows the X-ray powder diffraction pattern of an α-crystalline form of linaclotide.

In some embodiments, the α form linaclotide is characterized by an X-ray powder diffraction pattern substantially as shown in FIG. 6. In some embodiments, the α form linaclotide is characterized by an X-ray powder diffraction pattern comprising one or more peaks as provided in Table 2. In some embodiments, a crystalline form of linaclotide is provided, wherein the crystalline form has an X-ray powder diffraction pattern comprising peaks at about 5.7, about 7.7 and about 23.8+/−0.5 degrees 2θ and optionally one or more peaks at about 6.3, about 8.4, about 9.5, about 10.5, about 11.7, about 12.4, about 13.6, about 14.7, about 15.4, about 17.0, about 17.8, about 19.6, about 20.6, about 21.3, about 22.5, about 24.4, about 25.1, about 26.5, about 27.1, about 27.7, and/or about 28.7+/−0.5 degrees 2θ.

Figure 7:
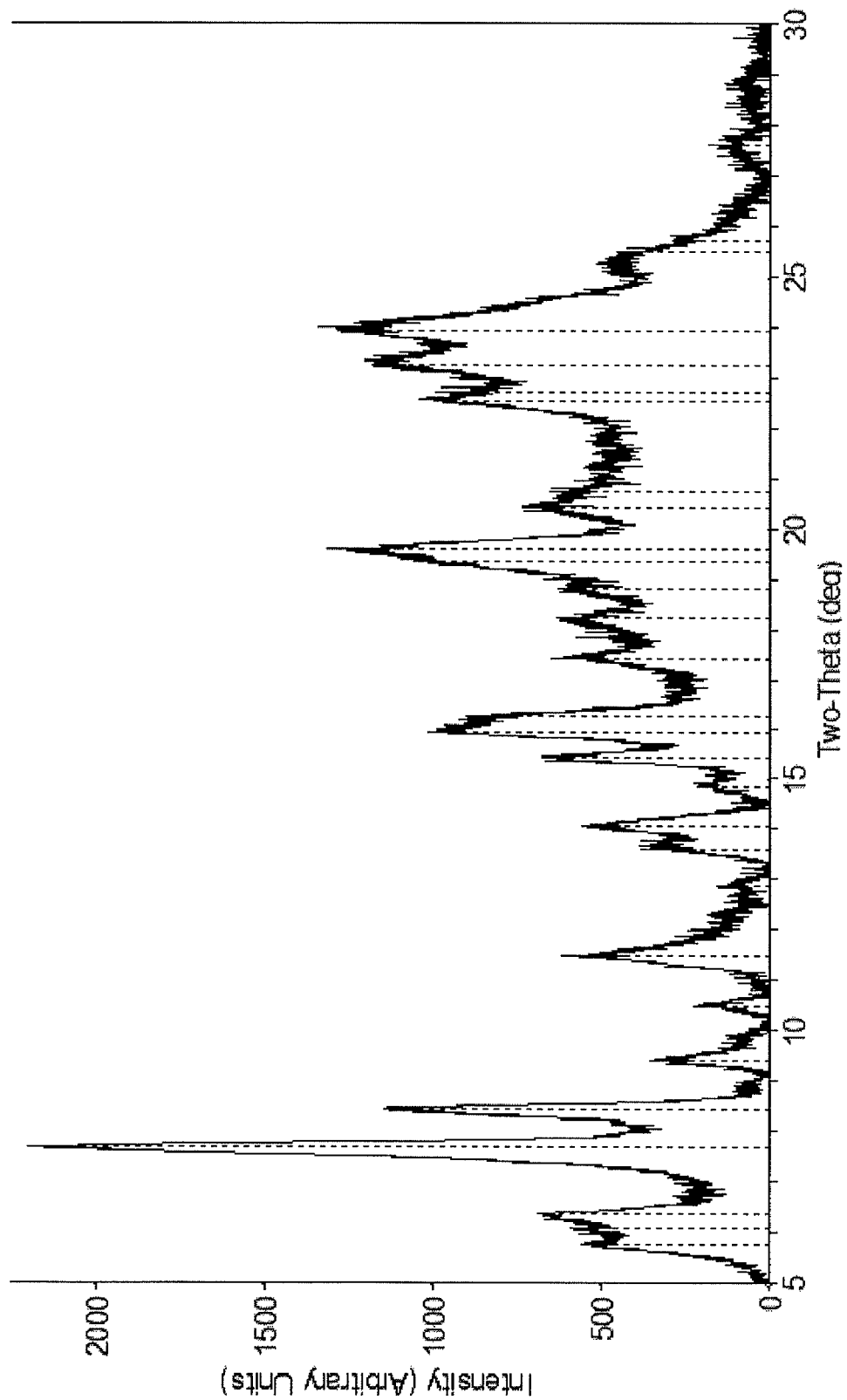
FIG. 7 shows the X-ray powder diffraction pattern of an α-crystalline form of linaclotide.

In some embodiments, the α form linaclotide is characterized by an X-ray powder diffraction pattern substantially as shown in FIG. 7. In some embodiments, a crystalline form of linaclotide is provided, wherein the crystalline form has an X-ray powder diffraction pattern comprising one or more peaks as provided in Table 3. In some embodiments, a crystalline form of linaclotide is provided, wherein the crystalline form has an X-ray powder diffraction pattern comprising peaks at about 5.8, about 7.7 and about 23.9+/−0.5 degrees 2θ and optionally one or more peaks at about 6.4, about 8.4, about 9.4, about 10.5, about 11.5, about 12.9, about 13.6, about 14.9, about 15.9, about 17.4, about 18.2, about 18.8, about 19.4, about 20.4, about 22.5, about 23.3 and/or about 25.7+/−0.5 degrees 2θ.

Figure 8:
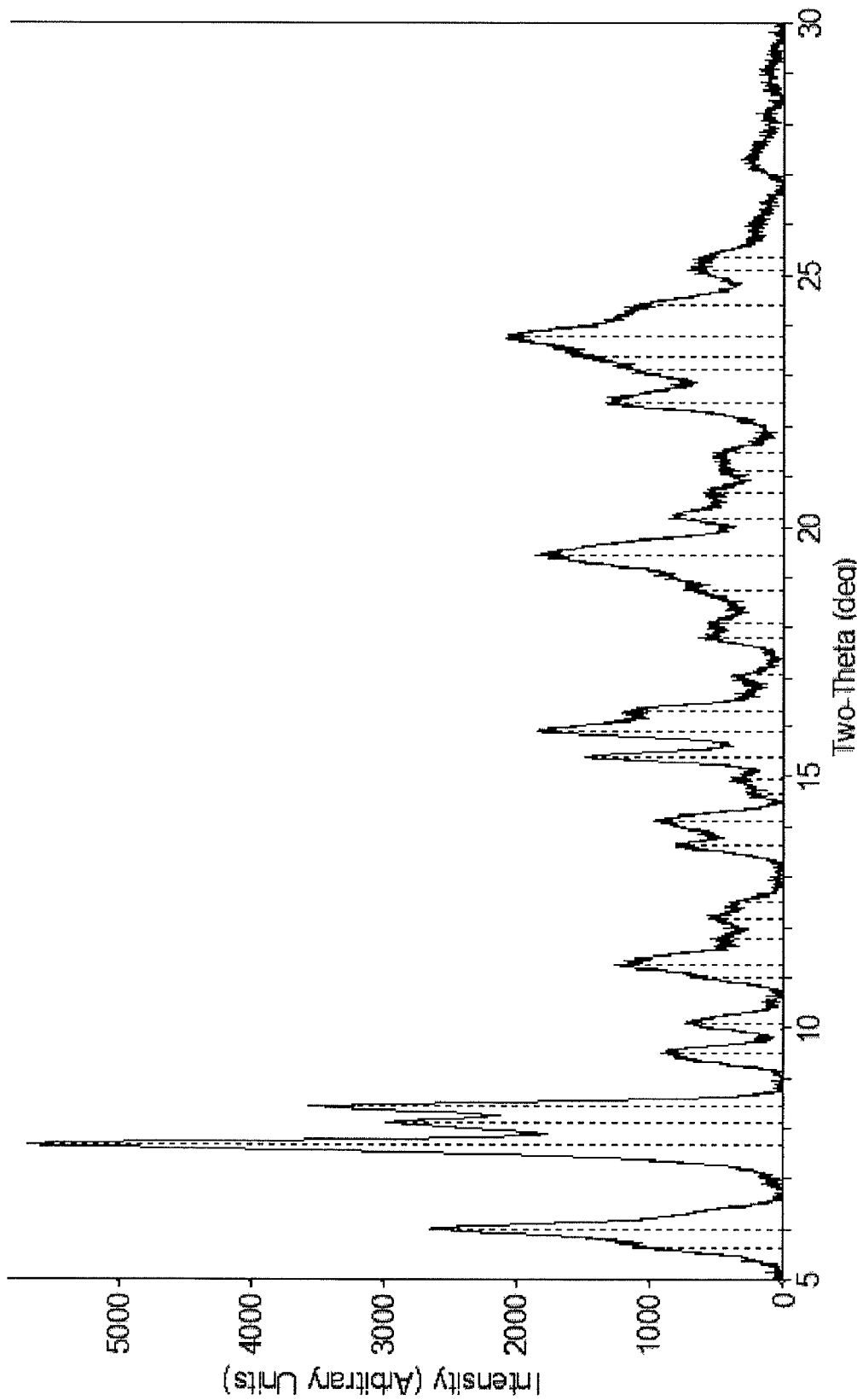
FIG. 8 shows the X-ray powder diffraction pattern of an α-crystalline form of linaclotide.

In some embodiments, the α form linaclotide is characterized by an X-ray powder diffraction pattern substantially as shown in FIG. 8. In some embodiments, a crystalline form of linaclotide is provided, wherein the crystalline form has an X-ray powder diffraction pattern comprising one or more peaks as provided in Table 4. In some embodiments, a crystalline form of linaclotide is provided, wherein the crystalline form has an X-ray powder diffraction pattern comprising one or more peaks at about 5.6, about 7.7, about 23.8 and optionally one or more peaks at about 8.4, about 9.5, about 10.1, about 11.0, about 11.8, about 12.2, about 14.1, about 14.9, about 15.4, about 16.3, about 17.0, about 17.8, about 18.7, about 19.4, about 20.7, about 21.5, about 22.5, about 24.4 and/or about 25.4+/−0.5 degrees 2θ.

Figure 9:
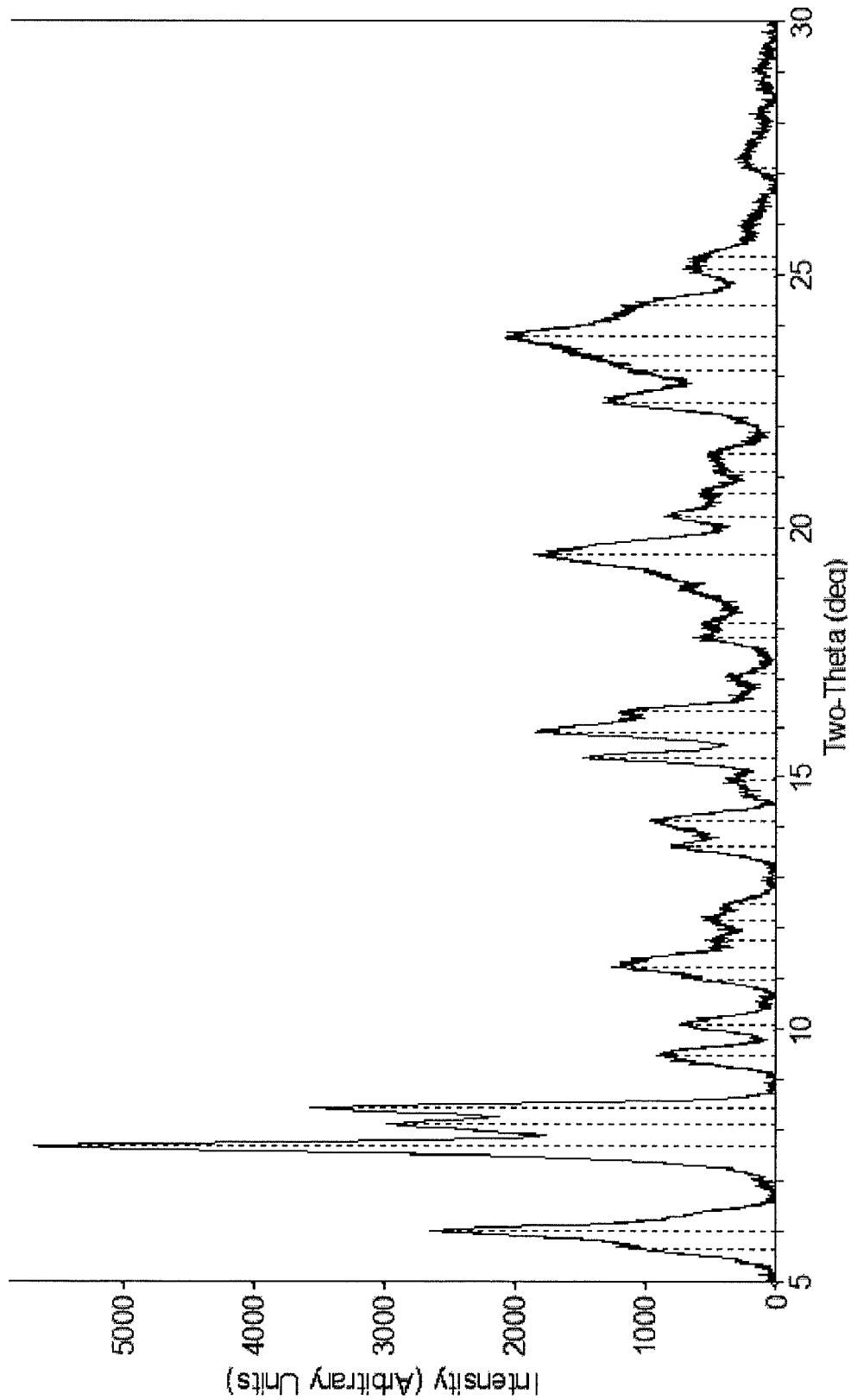
FIG. 9 shows the X-ray powder diffraction pattern of an α-crystalline form of linaclotide.

In some embodiments, the α form linaclotide is characterized by an X-ray powder diffraction pattern substantially as shown in FIG. 9. In some embodiments, a crystalline form of linaclotide is provided, wherein the crystalline form has an X-ray powder diffraction pattern comprising one or more peaks as provided in Table 5. In some embodiments, a crystalline form of linaclotide is provided, wherein the crystalline form has an X-ray powder diffraction pattern comprising peaks at about 7.7, about 23.8+/−0.5 degrees 2θ and optionally one or more peaks at about 5.6, about 9.5, about 10.1, about 11.0, about 11.8, about 12.5, about 14.1, about 14.9, about 15.9, about 17.0, about 17.8, about 19.4, about 20.2, about 20.7, about 21.1, about 21.5, about 22.5, about 23.1, about 24.4, about 25.4, and/or about 27.1+/−0.5 degrees 2θ.

Figure 10:
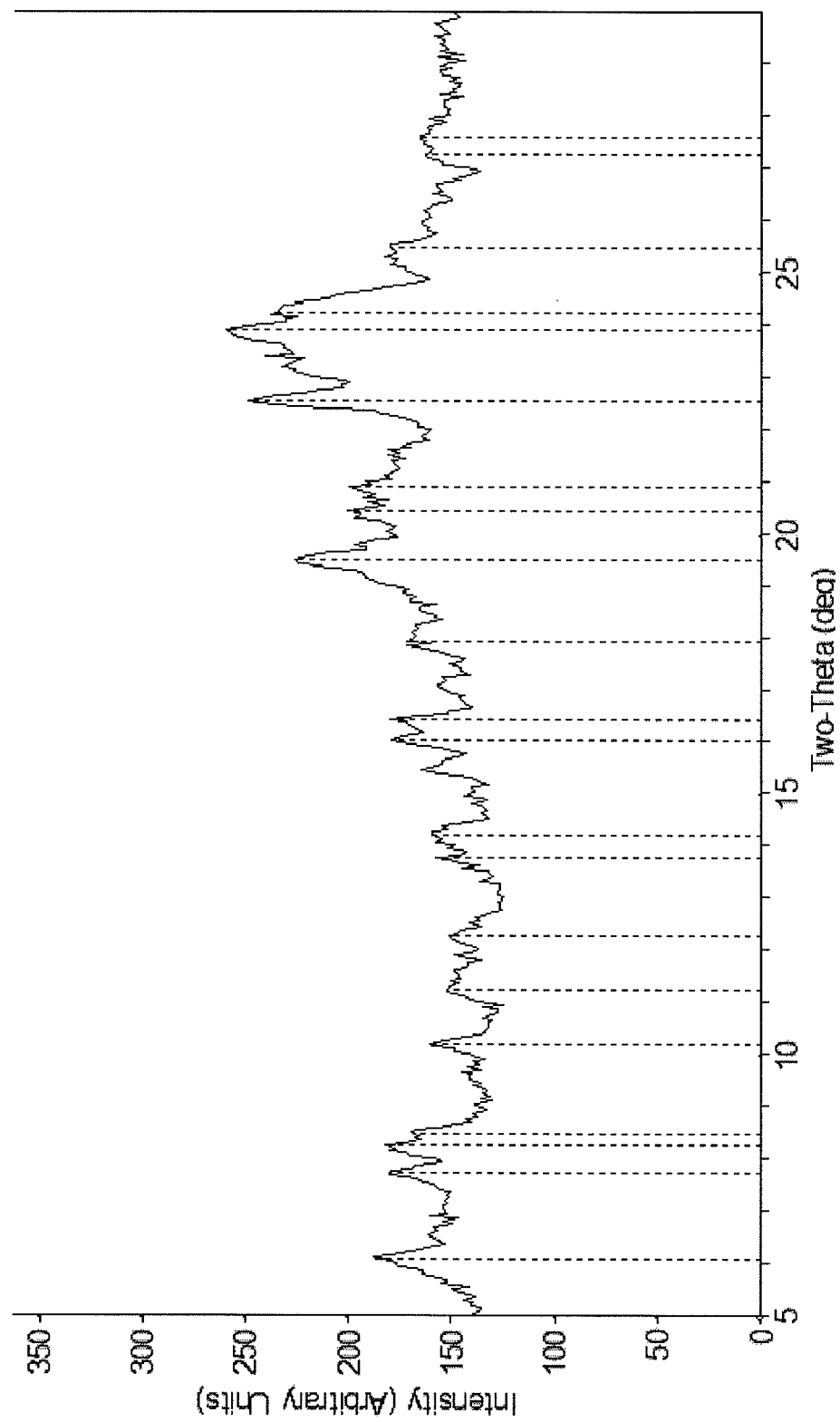
FIG. 10 shows the X-ray powder diffraction pattern of an α-crystalline form of linaclotide.

In some embodiments, the α form linaclotide is characterized by an X-ray powder diffraction pattern substantially as shown in FIG. 10. In some embodiments, a crystalline form of linaclotide is provided, wherein the crystalline form has an X-ray powder diffraction pattern comprising one or more peaks as provided in Table 6. In some embodiments, a crystalline form of linaclotide is provided, wherein the crystalline form has an X-ray powder diffraction pattern comprising peaks at about 5.6 and about 7.7+/−0.5 degrees 2θ and optionally one or more peaks at about 8.5, about 10.2, about 11.2, about 12.3, about 13.7, about 16.0, about 17.9, about 19.5, about 20.4, about 22.5, about 23.8 about 25.5, about 27.3, and/or about 27.6+/−0.5 degrees 2θ.

Figure 11:
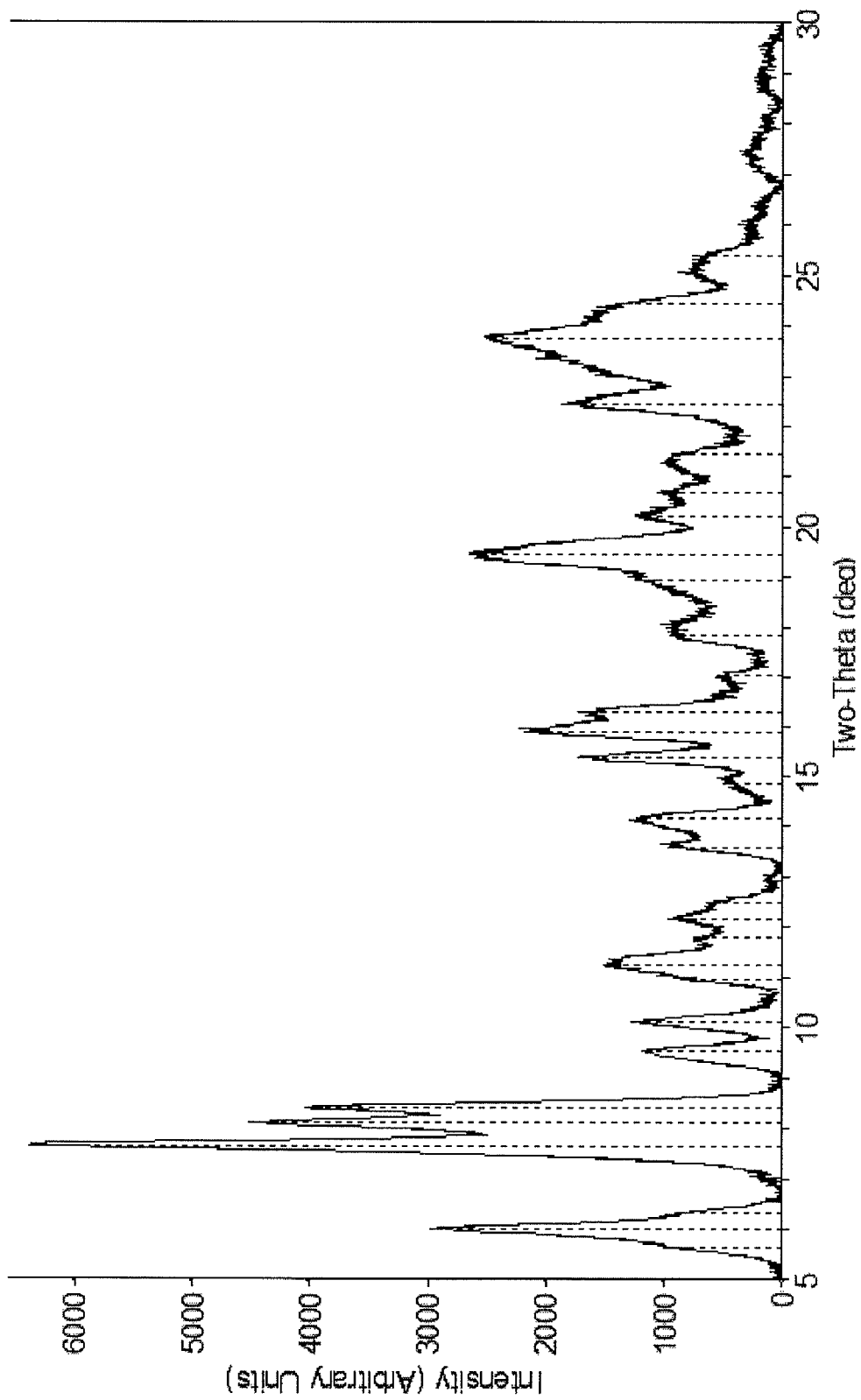
FIG. 11 shows the X-ray powder diffraction pattern of an α-crystalline form of linaclotide.

In some embodiments, the α form linaclotide is characterized by an X-ray powder diffraction pattern substantially as shown in FIG. 11. In some embodiments, a crystalline form of linaclotide is provided, wherein the crystalline form has an X-ray powder diffraction pattern comprising one or more peaks as provided in Table 7. In some embodiments, a crystalline form of linaclotide is provided, wherein the crystalline form has an X-ray powder diffraction pattern comprising one or more peaks at about 5.6, about 6.0, about 6.3, about 7.7, about 8.1, about 8.4, about 9.5, about 10.1, about 11.0, about 11.2, about 11.8, about 12.2, about 12.5, about 13.6, about 14.2, about 14.9, about 15.4, about 15.9, about 16.3, about 17.0, about 17.8, about 18.9, about 19.4, about 20.2, about 20.7, about 21.4, about 22.4, about 23.8, about 24.4 and/or about 25.4+/−0.5 degrees 2θ.

Figure 12:
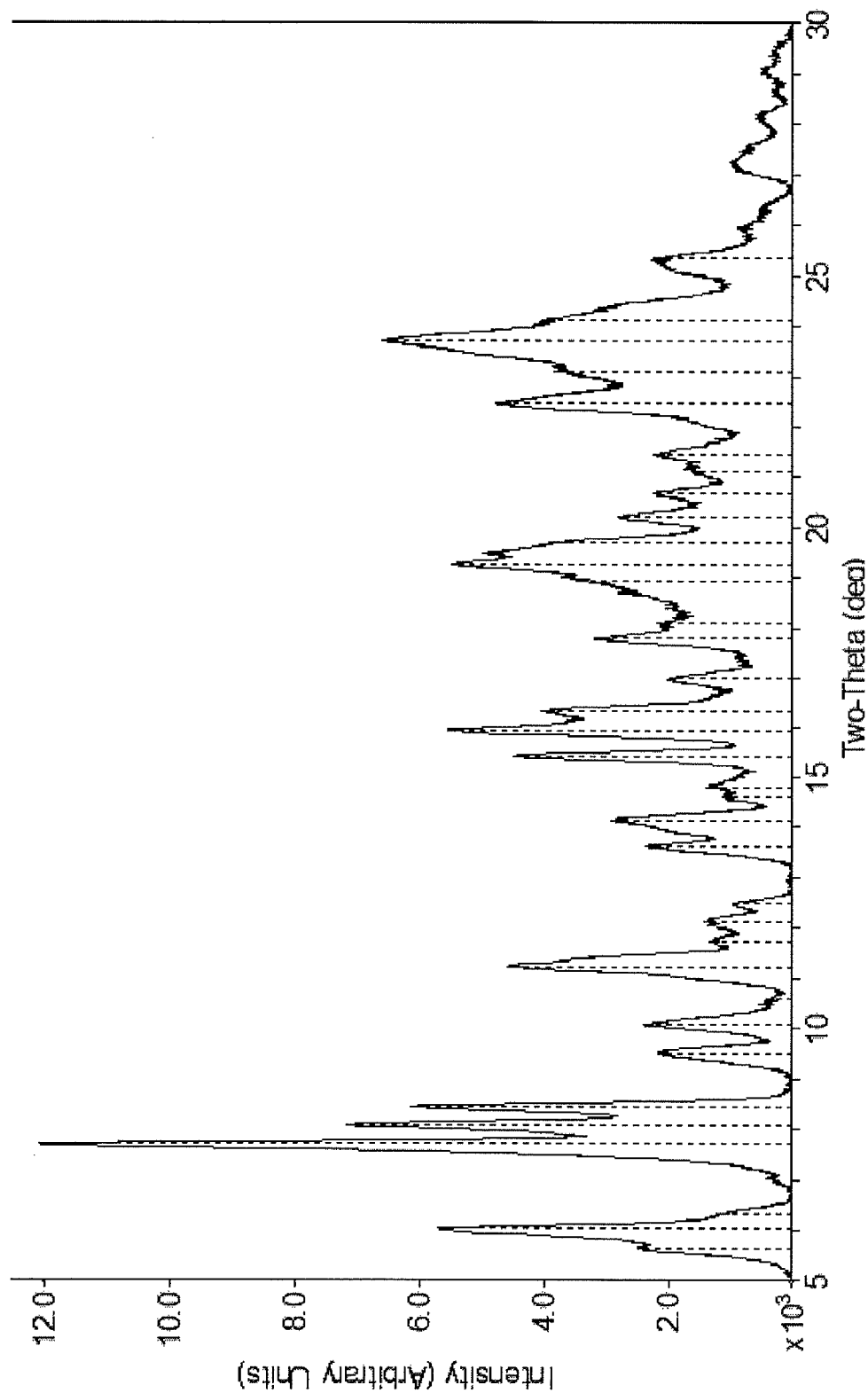
FIG. 12 shows the X-ray powder diffraction pattern of an α-crystalline form of linaclotide.

In some embodiments, the α form linaclotide is characterized by an X-ray powder diffraction pattern substantially as shown in FIG. 12. In some embodiments, a crystalline form of linaclotide is provided, wherein the crystalline form has an X-ray powder diffraction pattern comprising one or more peaks as provided in Table 8. In some embodiments, a crystalline form of linaclotide is provided, wherein the crystalline form has an X-ray powder diffraction pattern comprising one or more peaks at about 5.6, about 6.3, about 7.7, about 8.5, about 9.5, about 10.6, about 11.2, about 12.1, about 13.6, about 14.6, about 15.4, about 16.3, about 17.0, about 17.8, about 19.3, about 20.7, about 21.5, about 22.5, about 23.1, about 23.7 and/or about 25.3+/−0.5 degrees 2θ.

Figure 13:
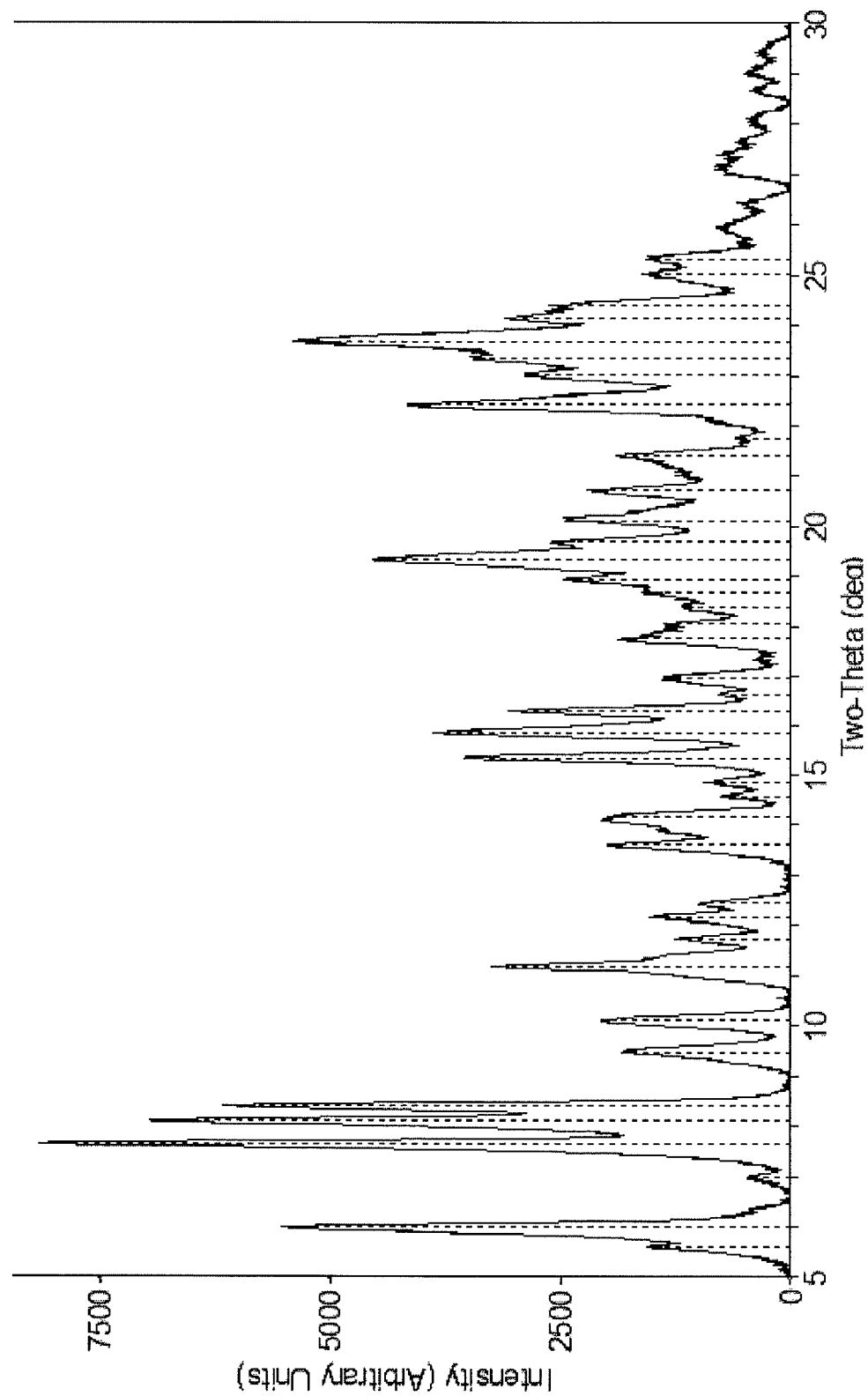
FIG. 13 shows the X-ray powder diffraction pattern of an α-crystalline form of linaclotide.

In some embodiments, the α form linaclotide is characterized by an X-ray powder diffraction pattern substantially as shown in FIG. 13. In some embodiments, a crystalline form of linaclotide is provided, wherein the crystalline form has an X-ray powder diffraction pattern comprising one or more peaks as provided in Table 9. In some embodiments, a crystalline form of linaclotide is provided, wherein the crystalline form has an X-ray powder diffraction pattern comprising one or more peaks at about 5.6, about 7.0, about 7.7, about 8.4, about 9.5, about 10.1, about 11.2, about 12.4, about 13.6, about 14.6, about 15.8, about 16.6, about 18.0, about 18.9, about 19.7, about 20.7, about 21.4, about 22.4, about 23.0, about 24.1 and/or about 25.0+/−0.5 degrees 2θ.

In some embodiments, α form linaclotide is characterized by an X-ray powder diffraction pattern comprising peaks having d-spacing values at about 3.7, about 11.5, and about 15.5+/−0.5 angstroms (Å). In some embodiments, α form linaclotide is characterized by an X-ray powder diffraction pattern comprising peaks having d-spacing values at about 3.7, about 4.5, about 11.5, and about 15.5+/−0.5 angstroms (Å).

In some embodiments, the X-ray powder diffraction peaks recited herein for particular embodiments can vary by ±0.4 degrees 2θ, by ±0.3 degrees 2θ, by ±0.2 degrees 2θ, or even by ±0.1 degrees 2θ. In some embodiments, for example, a crystalline form of linaclotide is provided having an X-ray power diffraction pattern comprising peaks at about 5.7, about 7.7 and about 23.8+/−0.3 degrees 2θ.

In some embodiments, α form linaclotide is characterized by an X-ray powder diffraction pattern comprising peaks having d-spacing values at about 1.4, about 1.1, about 1.0, about 0.9, about 0.8, about 0.6, about 0.5 and about 0.4+/−3% nm.

In some embodiments, the α form linaclotide is characterized by an X-ray powder diffraction pattern comprising d-spacing values at about 1.4, about 1.1, about 0.8, about 0.6, about 0.5 and about 0.4+/−3% nm.

In exemplary embodiments, the α form linaclotide is characterized by an X-ray powder diffraction pattern comprising a d-spacing value at about 1.4+/−3% nm.

In exemplary embodiments, the α form linaclotide is characterized by an X-ray powder diffraction pattern comprising a d-spacing value at about 1.1+/−3% nm.

In exemplary embodiments, the α form linaclotide is characterized by an X-ray powder diffraction pattern comprising a d-spacing value at about 1.0+/−3% nm.

In exemplary embodiments, the α form linaclotide is characterized by an X-ray powder diffraction pattern comprising a d-spacing value at about 0.9+/−3% nm.

In exemplary embodiments, the α form linaclotide is characterized by an X-ray powder diffraction pattern comprising a d-spacing value at about 0.8+/−3% nm.

In exemplary embodiments, the α form linaclotide is characterized by an X-ray powder diffraction pattern comprising a d-spacing value at about 0.6+/−3% nm.

In exemplary embodiments, the α form linaclotide is characterized by an X-ray powder diffraction pattern comprising a d-spacing value at about 0.5+/−3% nm.

In exemplary embodiments, the α form linaclotide is characterized by an X-ray powder diffraction pattern comprising a d-spacing value at about 0.4+/−3% nm.

Figure 4:
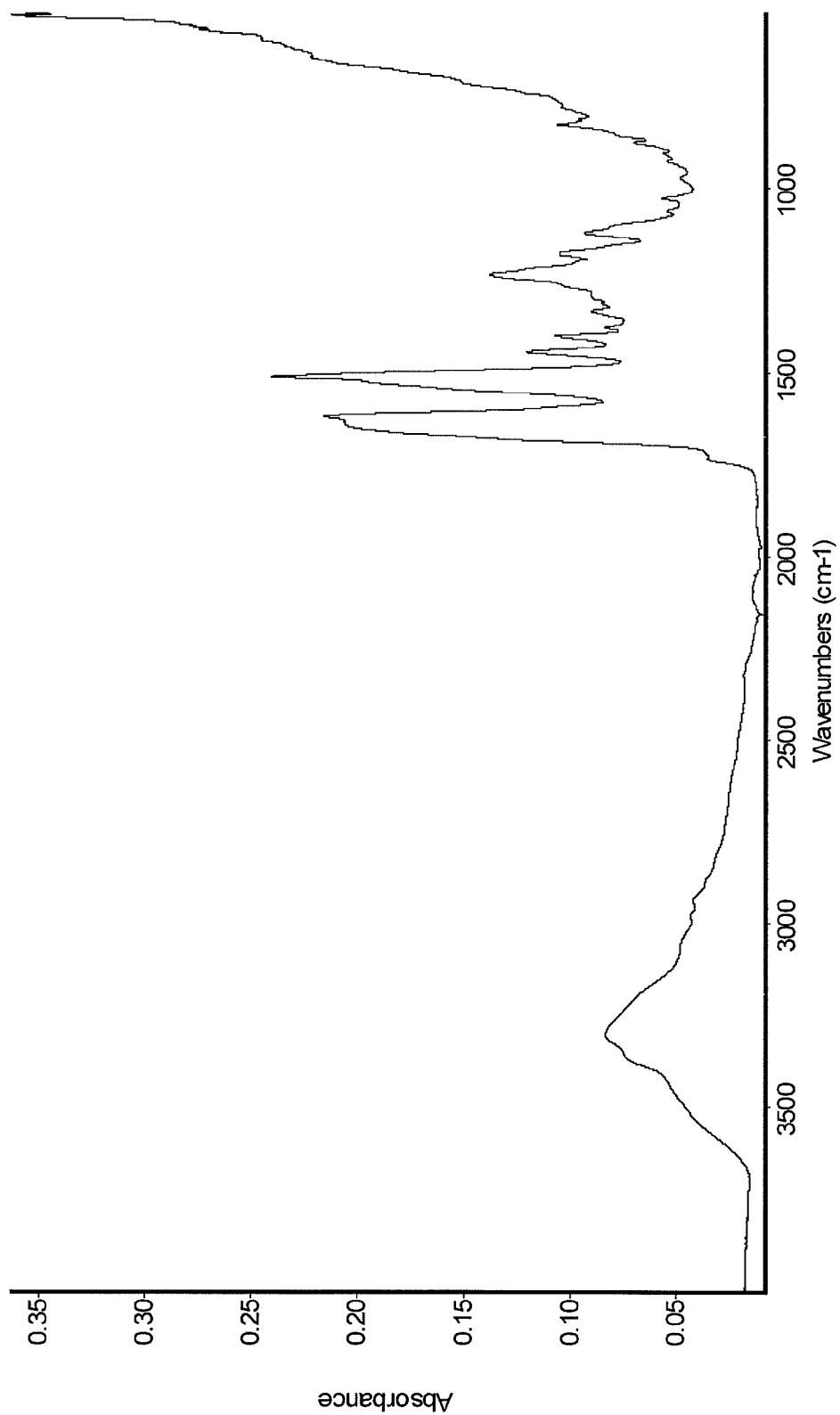
FIG. 4 shows the Fourier Transform infrared spectrum of an α-crystalline form of linaclotide.

In some embodiments, the α form linaclotide is characterized by a Fourier Transform infrared spectrum substantially as shown in FIG. 4.

Figure 5:
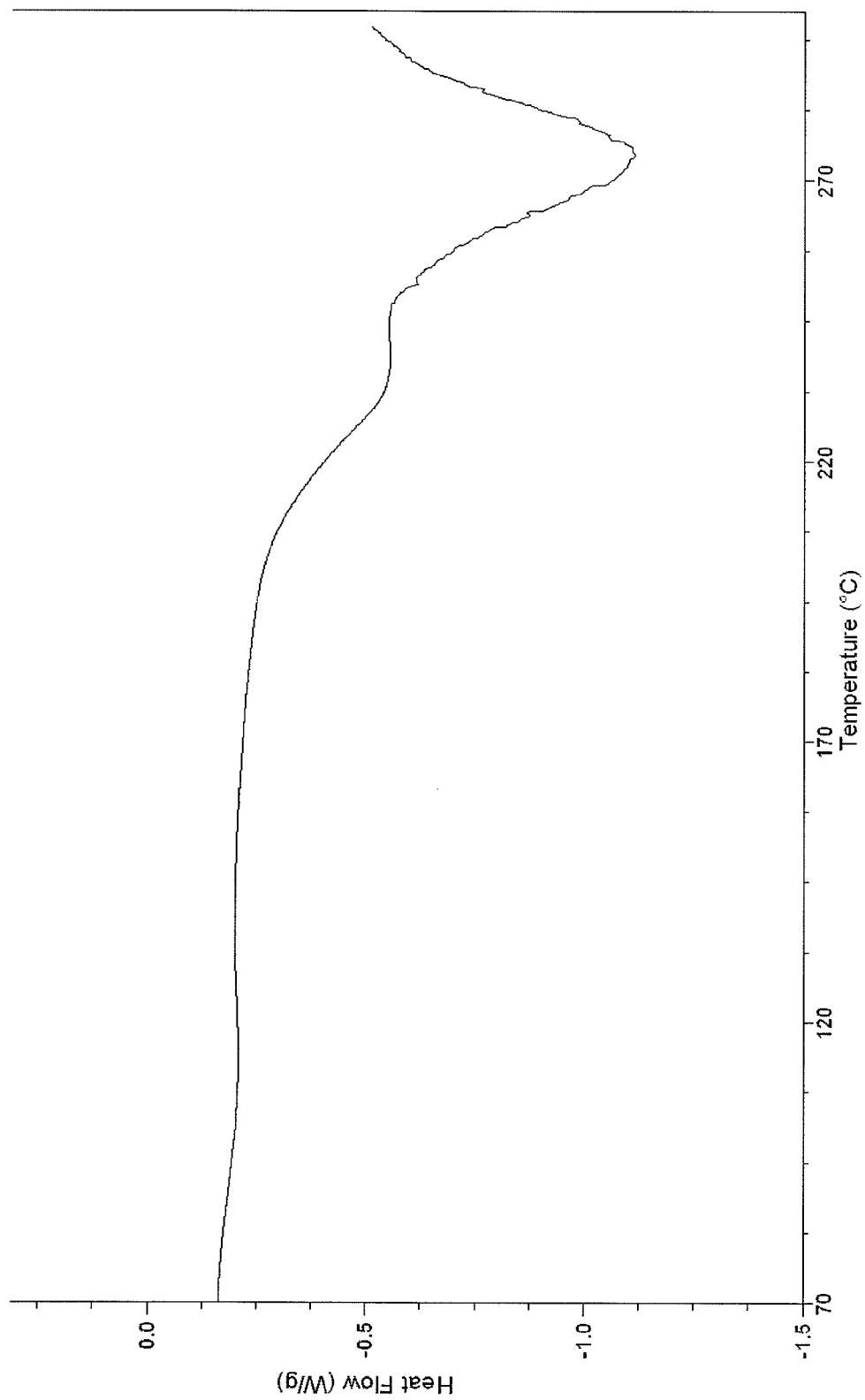
FIG. 5 shows a differential scanning calorimetry (DSC) thermogram of an α-crystalline form of linaclotide.

In some embodiments, the a form linaclotide is characterized by a DSC thermogram substantially as shown in FIG. 5.

In another aspect, the present invention provides processes for preparing the α-crystalline forms of linaclotide described herein. In some embodiments, methods for manufacturing a medicament comprising α form linaclotide that are useful in the treatment of a gastrointestinal disorder are provided. In some embodiments, for example, α form linaclotide is produced by crystallizing linaclotide to form α form linaclotide and optionally isolating the α form linaclotide. In some embodiments, α form linaclotide is prepared by crystallizing linaclotide in an aqueous acid solution and optionally isolating the α-crystalline form of linaclotide. Any suitable aqueous acid solution can be used in this regard, such as, for example, any solution of acid in water at various strengths or concentrations. Such acids may include, but are not limited to, hydrochloric acid, hydrobromic acid, sulfuric acid, nitric acid, methane sulfonic acid, phosphoric acid, acetic acid, lactic acid, p-toluene sulfonic acid, oxalic acid, glutamic acid, fumaric acid, malic acid, aspartic acid, ascorbic acid, benzoic acid, maleic acid and succinic acid. In some embodiments, the aqueous acid solution is selected from hydrochloric acid, hydrobromic acid, nitric acid, methane sulfonic acid, acetic acid, lactic acid, p-toluene sulfonic acid, oxalic acid, glutamic acid, aspartic acid, ascorbic acid, benzoic acid and succinic acid.

The α-crystalline form of linaclotide can be identified, distinguished, and separated from amorphous linaclotide in any suitable manner, such as on the basis of differences in the diffraction, thermal and/or spectroscopic properties of these different forms of linaclotide. Suitable such methods include, for example, X-ray powder diffractometry, capillary melting point determination, thermogravimetric analysis (TGA), differential scanning calorimetry (DSC) and/or spectroscopic methodologies (such as Raman spectroscopy and/or infrared (IR) spectroscopy).

One skilled in the art will understand that the relative intensities and positions of the peaks obtained by X-ray powder diffraction may vary depending upon, inter alia, the sample preparation technique, the sample mounting procedure, and the particular instrument employed. For example, in additional embodiments, the listed X-ray powder diffraction pattern peaks for the crystalline form of linaclotide is about +/−0.2 degrees 2θ.

The α form linaclotide can have any desired degree of purity, relative to other substances or components in the preparation. In one embodiment, the present invention provides an α-crystalline form of linaclotide that is substantially pure, such as, for example, having greater than 40%, greater than 50%, greater than 60%, greater than 70%, greater than 80%, greater than 85%, greater than 90%, greater than 95%, greater than 96%, greater than 97%, greater than 98%, greater than 99%, greater than 99.2%, greater than 99.4%, greater than 99.6%, greater than 99.6%, or even greater than 99.9% purity, relative to other substances or components in the preparation.

In exemplary embodiments, the α form linaclotide is about 45% to 95% pure, such as, for example, about 50% to 95% pure, about 55% to 90% pure, about 60% to 95% pure, or even about 70% to 99% pure, relative to other substances or components in the preparation. In some embodiments, the α form linaclotide is about 95% to 99% pure. In some embodiments, the α form linaclotide is about 90% to 95% pure. In some embodiments, the α form linaclotide is about 85% to 90% pure. In some embodiments, the α form linaclotide is about 80% to 85% pure. In some embodiments, the α form linaclotide is about 75% to 80% pure. In some embodiments, the α form linaclotide is about 70% to 75% pure. In certain embodiments, the α form linaclotide is about 65% to 70% pure. In some embodiments, the α form linaclotide is about 60% to 65% pure. In other embodiments, the α form linaclotide is about 55% to 60% pure. In yet other embodiments, the α form linaclotide is about 50% to 55% pure. In some embodiments, the α form linaclotide is about 45% to 50% pure.

Compositions

In some embodiments, the present invention provides a composition, formulation, or dosage form that comprises α form linaclotide and optional additional components, additives and/or species, such as, for example one or more ion species that interact with linaclotide.

Such additional components, additives, and/or species can be administered alone or as an active ingredient of the composition, formulation, or dosage form. Moreover, the additional components, additives, and/or species can be administered before, after, and/or concurrently with α form linaclotide.

In some embodiments, the additional components, additives, and/or species are administered separately to a patient or subject (e.g., in a separate formulation or dosage form) from the α form linaclotide.

In some embodiments, the optional additional components, additives, and/or species comprise an active component of the formulation.

In some embodiments, the optional components comprise one or more pharmaceutically-acceptable carriers and/or excipients.

In one aspect, the present invention provides a composition comprising α form linaclotide and a degradation product, such as a hydrolysis product, acetylation product, a formylation product, an oxidation product, a water-mediated degradation product, and/or a deamidation product.

The composition can contain any desired purity relative to hydrolysis product(s). In exemplary embodiments, the composition comprises less than about 10% by weight of hydrolysis product(s), relative to the total weight of the composition, such as, for example, less than about 7.5 wt. %, less than about 5 wt. %, or even less than about 2 wt. % of hydrolysis product(s). In some embodiments, the composition comprises from about 0.05% to about 5% by weight of hydrolysis product(s). In certain embodiments, the composition comprises from about 0.05% to about 2% by weight of the hydrolysis product(s). In certain embodiments, the composition may comprise from about 0.1% to about 2% by weight of the hydrolysis product(s).

Alternatively, or in addition, the composition can contain any desired purity relative to acetylation product(s). In exemplary embodiments, the acetylation product may comprise less than 10% by weight of the composition. In exemplary embodiments, the acetylation product may comprise less than 7.5% by weight of the composition. In exemplary embodiments, the acetylation product may comprise less than 5% by weight of the composition. In some embodiments, the acetylation product may comprise less than 2% by weight of the composition. In other embodiments, the acetylation product may comprise less than 1% by weight of the composition. In still other embodiments, the acetylation product may comprise less than 0.5% by weight of the composition. In some embodiments, the acetylation product may comprise from about 0.05% to about 5% by weight of the composition. In some embodiments, the acetylation product may comprise from about 0.05% to about 2% by weight of the composition. In other embodiments, the acetylation product may comprise from about 0.1% to about 2% by weight of the composition. In yet other embodiments, the acetylation product may comprise from about 0.1% to about 2% by weight of the composition.

Alternatively, or in addition, the composition can contain any desired purity relative to formylation product(s). In exemplary embodiments, the formylation product may comprise less than 10% by weight of the composition. In exemplary embodiments, the formylation product may comprise less than 7.5% by weight of the composition. In exemplary embodiments, the formylation product may comprise less than 5% by weight of the composition. In some embodiments, the formylation product may comprise less than 2% by weight of the composition. In other embodiments, the formylation product may comprise from about 0.05% to about 5% by weight of the composition. In some embodiments, the formylation product may comprise from about 0.05% to about 2% by weight of the composition. In other embodiments, the formylation product may comprise from about 0.1% to about 2% by weight of the composition.

Alternatively, or in addition, the composition can contain any desired purity relative to oxidation product(s). In some embodiments, the oxidation product may comprise less than 10% by weight of the composition. In some embodiments, the oxidation product may comprise less than 7.5% by weight of the composition. In some embodiments, the oxidation product may comprise less than 5% by weight of the composition. In other embodiments, the oxidation product may comprise less than 2% by weight of the composition. In still other embodiments, the oxidation product may comprise from about 0.05% to about 5% by weight of the composition. In exemplary embodiments, the oxidation product may comprise from about 0.05% to about 2% by weight of the composition. In yet other embodiments, the oxidation product may comprise from about 0.1% to about 2% by weight of the composition.

Alternatively, or in addition, the composition can contain any desired purity relative to water-mediated degradation product(s). In some embodiments, the water-mediated degradation product(s) may comprise less than 10% by weight of the composition. In some embodiments, the water-mediated degradation product(s) may comprise less than 7.5% by weight of the composition. In some embodiments, the water-mediated degradation product(s) may comprise less than 5% by weight of the composition. In other embodiments, the water-mediated degradation product(s) may comprise less than 2% by weight of the composition. In still other embodiments, the water-mediated degradation product(s) may comprise from about 0.05% to about 5% by weight of the composition. In exemplary embodiments, the water-mediated degradation product(s) may comprise from about 0.05% to about 2% by weight of the composition. In yet other embodiments, the water-mediated degradation product(s) may comprise from about 0.1% to about 2% by weight of the composition.

Alternatively, or in addition, the composition can contain any desired purity relative to deamidation product(s). In some embodiments, the deamidation product may comprise less than 10% by weight of the composition. In some embodiments, the deamidation product may comprise less than 7.5% by weight of the composition. In some embodiments, the deamidation product may comprise less than 5% by weight of the composition. In other embodiments, the deamidation product may comprise less than 2% by weight of the composition. In still other embodiments, the deamidation product may comprise from about 0.05% to about 5% by weight of the composition. In exemplary embodiments, the deamidation product may comprise from about 0.05% to about 2% by weight of the composition. In yet other embodiments, the deamidation product may comprise from about 0.1% to about 2% by weight of the composition.

In another aspect, the invention provides a composition comprising α form linaclotide and less than 10 wt. % (such as less than 8 wt. %, less than 6 wt. %, less than 5 wt. %, less than 4 wt. %, less than 3 wt. %, less than 2 wt. %, less than 1 wt. %, less than 0.5 wt. %, or even less than 0.25 wt. %) of a combined total of a degradation product, such as a hydrolysis product, a formylation product, an oxidation product, a water-mediated degradation product, and/or a deamidation product.

In another aspect, the invention provides a composition comprising α form linaclotide and less than 20 wt. % (such as less than 18 wt. %, less than 16 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, less than 0.5 wt. %, or even less than 0.25 wt. %) of a combined total of a degradation product, such as a hydrolysis product, an acetylation product, a formylation product, an oxidation product, a water-mediated degradation product, and/or a deamidation product.

In one aspect, the present invention provides a composition comprising α form linaclotide and multimers. In some embodiments, the multimers may be formed due to disulfide linkages. In some embodiments, the multimers may be formed due to non-disulfide linkages. In some embodiments, the composition may contain any desired purity relative to multimers. In some embodiments, the composition comprises less than about 20 wt. % of multimers, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or even less than about 0.1 wt. % of multimers.

In some embodiments, the compositions may comprise α form linaclotide and a dimer. In some embodiments, the composition comprises less than about 20 wt. % of dimers, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or even less than about 0.1 wt. % of dimers.

In another aspect, the present invention provides a composition comprising α form linaclotide and an isomer. In some embodiments, the composition comprises less than about 20 wt. % of isomers, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or even less than about 0.1 wt. % of isomers.

In one aspect, the present invention provides a composition comprising α form linaclotide and less than about 40 wt %, such as less than about 30 wt. %, less than about 20 wt. %, less than about 15 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, less than about 0.1 wt. %, or even less than about 0.01 wt. % of amorphous linaclotide.

In exemplary embodiments, the present invention provides a composition comprising between about 50:50 and 99:1 α form linaclotide to amorphous linaclotide, such as, for example, between about 55:45 and 95:5 α form linaclotide to amorphous linaclotide, between about 60:40 and 90:10 α form linaclotide to amorphous linaclotide, between about 70:30 and 85:15 α form linaclotide to amorphous linaclotide, or even between about 75:25 and 99:1 α form linaclotide to amorphous linaclotide.

Formulations and preparations that comprise the α form linaclotide described herein can be prepared in any suitable manner, such as described, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the present invention can be accomplished in any suitable manner according to patient needs, for example, orally, nasally, parenterally (e.g., subcutaneously, intravenously, intramuscularly, intrasternally, and/or by infusion), by inhalation, rectally, vaginally, topically, and/or by ocular administration.

Various dosage forms can be used for administering the present invention, such as any suitable oral dosage forms (e.g., solid oral dosage forms). In particular, for example, the present invention can be administered in the form of tablets, gelcaps, capsules, caplets, granules, lozenges and bulk powders. α form linaclotide can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering α form linaclotide, including aqueous and nonaqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The α form linaclotide may be injected, for example, intravenously, in the form of an isotonic sterile solution.

Suppositories for rectal administration of α form linaclotide can be prepared by mixing the compound with a suitable excipient such as cocoa butter, salicylates and polyethylene glycols.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

Methods of Treatment

The present invention provides methods of treating gastrointestinal disorders in a patient (e.g., mammal or human) diagnosed with one or more gastrointestinal disorders (such as, for example, irritable bowel syndrome, constipation-predominant irritable bowel syndrome, chronic constipation, opioid induced constipation and/or dyspepsia), wherein the method comprises administering an effective amount of a form linaclotide (or a composition comprising said α form linaclotide and optional additional components, additives, and/or species, as described herein) to said patient.

In exemplary embodiments, the methods comprise administering a pharmaceutical composition comprising α form linaclotide and a pharmaceutically acceptable carriers and/or excipients.

In exemplary embodiments, the methods comprise administering a pharmaceutical composition comprising α form linaclotide and a degradation product.

In exemplary embodiments, the methods comprise administering a pharmaceutical composition comprising α form linaclotide and a hydrolysis product.

In exemplary embodiments, the methods comprise administering a pharmaceutical composition comprising α form linaclotide and an acetylation product.

In exemplary embodiments, the methods comprise administering a pharmaceutical composition comprising α form linaclotide and an oxidation product.

In exemplary embodiments, the methods comprise administering a pharmaceutical composition comprising α form linaclotide and a formylation product.

In exemplary embodiments, the methods comprise administering a pharmaceutical composition comprising α form linaclotide and a deamidation product.

In exemplary embodiments, the methods comprise administering a pharmaceutical composition comprising α form linaclotide and a multimer product.

In exemplary embodiments, the methods comprise administering a pharmaceutical composition comprising α form linaclotide and a dimer product.

In exemplary embodiments, the methods comprise administering a pharmaceutical composition comprising α form linaclotide and an isomer product.

An effective amount of α form linaclotide required to achieve desired results (such as desired treatment and/or symptom relief) of a subject is dependent on several understood factors, such as the identity and severity of the disorder being treated, as well as the age, weight, etc., of the patient being treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of the invention may be used in combination with other drugs or therapies that are used in the treatment/prevention/suppression and/or amelioration of the diseases or conditions for which compounds of the invention are useful.

Such other drug(s) may be administered, by a route and in an amount commonly used therefore, contemporaneously or sequentially with a compound of the invention. When a compound of the present invention is used contemporaneously with one or more other drugs, a pharmaceutical unit dosage form containing such other drugs in addition to the compound of the invention may be employed. Accordingly, the pharmaceutical compositions of the present invention include those that also contain one or more other active ingredients, in addition to a compound of invention.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Example 1

Preparation of α-Crystalline Form of Linaclotide

Example 1A 100 mg linaclotide was added to 10 ml aqueous acid solution (for example, 0.1N hydrochloric acid). The mixture was stirred using magnetic stirrer for 30-60 minutes at room temperature. The suspension was carefully filtered into a glass container and the filtrate was stored under room temperature conditions. After a suitable formation period, the α crystalline form of linaclotide was carefully isolated, washed, dried and analyzed using powder X-ray diffractometry. FIG. 2 shows the X-ray diffraction pattern for the α crystalline form of linaclotide.

Example 1B 100 mg linaclotide was added to 10 ml aqueous acid solution (for example, 0.1N hydrochloric acid). The mixture was stirred using magnetic stirrer for 10-60 minutes at temperature in the range of 20° C. to 65° C. The suspension was carefully filtered into a glass container and the filtrate was stored under room temperature conditions. After a suitable formation period, the crystalline form of linaclotide was carefully isolated, washed, dried and analyzed using powder X-ray diffractometry.

Example 1C 100 mg linaclotide was added to 10 ml aqueous acid solution (for example, 0.1N hydrochloric acid). The mixture was stirred using magnetic stirrer for 10-60 minutes at temperature in the range of 20° C. to 65° C. The suspension was carefully filtered into a glass container and the filtrate was stored at 4° C. After a suitable formation period, the crystalline form of linaclotide was carefully isolated, washed, dried and analyzed using powder X-ray diffractometry.

Example 1D 100 mg linaclotide was added to 10 ml aqueous acid solution (for example, 0.1N hydrochloric acid). The mixture was stirred using magnetic stirrer for 10-60 minutes at temperature in the range of 20° C. to 65° C. The suspension was carefully filtered into a glass container. A weighed amount of a salt (for example sodium chloride) was added to the filtrate and it was stored under room temperature conditions. After a suitable formation period, the crystalline form of linaclotide was carefully isolated, washed, dried and analyzed using powder X-ray diffractometry.

Example 1E 100 mg linaclotide was added to 10 ml aqueous acid solution (for example, 0.1N hydrochloric acid). The mixture was stirred using magnetic stirrer for 10-60 minutes at temperature in the range of 20° C. to 65° C. The suspension was carefully filtered into a glass container. A weighed amount of a salt (for example sodium chloride) was added to the filtrate and it was stored at 4° C. After a suitable formation period, the crystalline form of linaclotide was carefully isolated, washed, dried and analyzed using powder X-ray diffractometry.

Example 1F 100 mg linaclotide was added to 10 ml aqueous acid solution (for example, 0.1N hydrochloric acid) containing a known amount of polymer (for example, polyvinyl pyrrolidone). The mixture was shaken using an end-over-end shaker for 6-48 hours at temperature in the range of 20° C. to 65° C. The suspension was carefully filtered into a glass container. A weighed amount of a salt (for example sodium chloride) was added to the filtrate and it was stored at 4° C. After a suitable formation period, the crystalline form of linaclotide was carefully isolated, washed, dried and analyzed using powder X-ray power.

The X-ray power diffraction patterns of the samples were determined in Example 1 using a wide-angle bench-top X-ray diffractometer (MiniFlex, Rigaku/MSC Inc., Woodlands, Tex.). The samples were loaded on zero background holders and exposed to CuKα radiation (30 kV×15 mA). The instrument was operated in the step-scan mode, in increments of 0.05°2θ. The angular range was 5 to 40°2θ, and the scan rate was 0.1°2θ/min. The data collection and analyses were performed with commercially available software (JADE, version 7.1, Materials Data, Inc., Livermore, Calif.).

Example 2

XRPD Analysis of α-Crystalline Form of Linaclotide

The α-crystalline forms of linaclotide that were prepared in Examples 1A-1F were prepared and analyzed in this Example using a second wide-angle bench-top X-ray diffractometer (Model D8, Bruker AXS Inc., Madison Wis.). A small amount of the samples was loaded on a zero background holder and exposed to CuKα radiation (40 kV×40 mA) in the wide-angle bench-top X-ray diffractometer (Model D8, Bruker AXS Inc., Madison Wis.). The instrument was operated in the step-scan mode, in increments of 0.05°2θ. The angular range was 5 to 30°2θ, and the scan rate ranged from 0.05-0.1°2θ/min. The data collection and analyses were performed with commercially available software (JADE, version 7.1, Materials Data, Inc., Livermore, Calif.).

Example 2A 100 mg linaclotide was mixed with 0.1N hydrochloric acid. The mixture was stirred using magnetic stirrer for 30-60 minutes at room temperature. The suspension was carefully filtered into a glass container and the filtrate was stored under room conditions. After a suitable formation period, the α crystalline form of linaclotide was carefully isolated, washed, dried and analyzed using powder X-ray diffractometry. FIG. 3 shows the X-ray powder diffraction pattern for the crystalline form of linaclotide. Peak positions for the XRD are provided in Table 1.

TABLE 1

| 2-Theta (°) | d(Å) |
|---|---|
| 5.7 | 15.6 |
| 6.1 | 14.6 |
| 7.0 | 12.5 |
| 7.7 | 11.4 |
| 8.2 | 10.8 |
| 8.5 | 10.4 |
| 9.6 | 9.2 |
| 10.2 | 8.7 |
| 11.0 | 8.0 |
| 11.3 | 7.8 |
| 11.8 | 7.5 |
| 12.2 | 7.2 |
| 12.6 | 7.0 |
| 13.7 | 6.5 |
| 14.3 | 6.2 |
| 15.0 | 5.9 |
| 15.5 | 5.7 |
| 16.0 | 5.5 |
| 16.4 | 5.4 |
| 17.1 | 5.2 |
| 17.9 | 4.9 |
| 18.5 | 4.8 |
| 19.0 | 4.7 |
| 19.4 | 4.6 |
| 19.8 | 4.5 |
| 20.3 | 4.4 |
| 20.8 | 4.3 |
| 21.5 | 4.1 |

TABLE 1-continued

| 2-Theta (°) | d(Å) |
|---|---|
| 22.5 | 3.9 |
| 23.1 | 3.8 |
| 23.8 | 3.7 |
| 24.2 | 3.7 |
| 24.5 | 3.6 |
| 25.5 | 3.5 |
| 26.1 | 3.4 |
| 26.5 | 3.4 |
| 27.5 | 3.2 |
| 28.2 | 3.2 |
| 28.8 | 3.1 |
| 29.2 | 3.1 |
| 29.6 | 3.0 |

The α form linaclotide was also analyzed via Fourier Transform infrared spectroscopy by loading a small sample of the α form linaclotide (approx. 1 mg) onto a Durascope™ diamond stage and exposing it to an IR beam in the FT-IR spectrometer using attenuated total diffuse reflectance (ATR) mode. All spectra were run at 4000-525 $cm^{-1}$ wavenumbers, 300 scans and 2 $cm^{-1}$ resolution. The Fourier Transform infrared spectrum for the α form linaclotide is shown in FIG. 4.

The α form linaclotide was also analyzed using a differential scanning calorimeter (MDSC Q1000, TA Instruments, New Castle, Del.) with a refrigerated cooling accessory. The instrument was calibrated with pure samples of indium. About 2-5 mg sample was weighed in open non-hermetic aluminum pans with a cover lid and heated under dry nitrogen purge (flow rate 50 ml/min) at 10° C./min. The data was analyzed using Universal Analysis 2000 (TA instruments, New Castle, Del.). The DSC thermogram of the α form linaclotide is shown in FIG. 5.

Example 2B 100 mg linaclotide was mixed with 0.1N hydrochloric acid. The mixture was stirred using magnetic stirrer for 10-60 minutes at temperature in the range of 20° C. to 65° C. The suspension was carefully filtered into a glass container and the filtrate was stored under room conditions. After a suitable formation period, the α crystalline form of linaclotide was carefully isolated, washed, dried and analyzed using powder X-ray diffractometry. FIG. 6 shows the X-ray powder diffraction pattern for the crystalline form of linaclotide. Peak positions for the XRD are provided in Table 2.

TABLE 2

| 2-Theta (°) | d(Å) |
|---|---|
| 5.7 | 15.5 |
| 6.0 | 14.6 |
| 6.3 | 14.0 |
| 7.7 | 11.5 |
| 8.1 | 10.9 |
| 8.4 | 10.5 |
| 9.0 | 9.9 |
| 9.5 | 9.3 |
| 10.1 | 8.8 |
| 10.5 | 8.4 |
| 10.9 | 8.1 |
| 11.4 | 7.8 |
| 11.7 | 7.6 |
| 12.1 | 7.3 |
| 12.4 | 7.1 |
| 12.9 | 6.8 |
| 13.6 | 6.5 |
| 14.2 | 6.2 |
| 14.7 | 6.0 |
| 14.9 | 5.9 |
| 15.4 | 5.8 |
| 15.9 | 5.6 |
| 17.0 | 5.2 |
| 17.8 | 5.0 |
| 18.1 | 4.9 |
| 19.6 | 4.5 |
| 20.2 | 4.4 |
| 20.6 | 4.3 |
| 21.3 | 4.2 |
| 22.5 | 3.9 |
| 23.8 | 3.7 |
| 24.4 | 3.6 |
| 25.1 | 3.5 |
| 26.0 | 3.4 |
| 26.5 | 3.4 |
| 27.1 | 3.3 |
| 27.7 | 3.2 |
| 28.7 | 3.1 |

Example 2C 100 mg linaclotide was mixed with 0.1N hydrochloric acid. The mixture was stirred using magnetic stirrer for 10-60 minutes at temperature in the range of 20° C. to 65° C. The suspension was carefully filtered into a glass container and the filtrate was stored at 4° C. After a suitable formation period, the α crystalline form of linaclotide was carefully isolated, washed, dried and analyzed using powder X-ray diffractometry. FIG. 7 shows the X-ray powder diffraction pattern for the crystalline form of linaclotide. Peak positions for the XRD are provided in Table 3.

TABLE 3

| 2-Theta (°) | d(Å) |
|---|---|
| 5.8 | 15.3 |
| 6.1 | 14.5 |
| 6.4 | 13.9 |
| 7.7 | 11.5 |
| 8.4 | 10.5 |
| 9.4 | 9.4 |
| 10.5 | 8.4 |
| 11.5 | 7.7 |
| 12.9 | 6.9 |
| 13.6 | 6.5 |
| 14.1 | 6.3 |
| 14.9 | 6.0 |
| 15.4 | 5.7 |
| 15.9 | 5.6 |
| 16.2 | 5.5 |
| 17.4 | 5.1 |
| 18.2 | 4.9 |
| 18.8 | 4.7 |
| 19.4 | 4.6 |
| 19.6 | 4.5 |
| 20.4 | 4.3 |
| 20.7 | 4.3 |
| 22.5 | 3.9 |
| 22.7 | 3.9 |
| 23.3 | 3.8 |
| 23.9 | 3.7 |
| 25.5 | 3.5 |
| 25.7 | 3.5 |
| 27.6 | 3.5 |

Example 2D 100 mg linaclotide was mixed with 0.1N hydrochloric acid. The mixture was stirred using magnetic stirrer for 10-60 minutes at temperature in the range of 20° C. to 65° C. The suspension was carefully filtered into a glass container. A weighed amount of sodium chloride was added to the filtrate and it was stored under room conditions. After a suitable formation period, the α crystalline form of linaclotide was carefully isolated, washed, dried and analyzed using powder X-ray diffractometry. FIG. 8 shows the X-ray powder diffraction pattern for the crystalline form of linaclotide. Peak positions for the XRD are provided in Table 4.

TABLE 4

| 2-Theta (°) | d(Å) |
| --- | --- |
| 5.6 | 15.6 |
| 6.0 | 14.7 |
| 7.7 | 11.5 |
| 8.1 | 10.9 |
| 8.4 | 10.5 |
| 9.5 | 9.3 |
| 10.1 | 8.8 |
| 11.0 | 8.0 |
| 11.2 | 7.9 |
| 11.8 | 7.5 |
| 12.2 | 7.3 |
| 12.5 | 7.1 |
| 13.6 | 6.5 |
| 14.1 | 6.3 |
| 14.6 | 6.0 |
| 14.9 | 5.9 |
| 15.4 | 5.8 |
| 15.9 | 5.6 |
| 16.3 | 5.4 |
| 17.0 | 5.2 |
| 17.8 | 5.0 |
| 18.1 | 4.9 |
| 18.7 | 4.7 |
| 19.4 | 4.6 |
| 20.2 | 4.4 |
| 20.7 | 4.3 |
| 21.1 | 4.2 |
| 21.5 | 4.1 |
| 22.5 | 4.0 |
| 23.1 | 3.8 |
| 23.4 | 3.8 |
| 23.8 | 3.7 |
| 24.4 | 3.6 |
| 25.1 | 3.5 |
| 25.4 | 3.5 |

Example 2E 100 mg linaclotide was mixed with 0.1N hydrochloric acid. The mixture was stirred using magnetic stirrer for 10-60 minutes at temperature in the range of 20° C. to 65° C. The suspension was carefully filtered into a glass container. A weighed amount of sodium chloride was added to the filtrate and it was stored at 4° C. After a suitable formation period, the α crystalline form of linaclotide was carefully isolated, washed, dried and analyzed using powder X-ray diffractometry. FIG. 9 shows the X-ray powder diffraction pattern for the crystalline form of linaclotide. Peak positions for the XRD are provided in Table 5.

TABLE 5

| 2-Theta (°) | d(Å) |
| --- | --- |
| 5.6 | 15.6 |
| 6.0 | 14.7 |
| 7.7 | 11.5 |
| 8.1 | 10.9 |
| 8.4 | 10.5 |
| 9.5 | 9.3 |

TABLE 5-continued

| 2-Theta (°) | d(Å) |
| --- | --- |
| 10.1 | 8.8 |
| 11.0 | 8.0 |
| 11.2 | 7.9 |
| 11.8 | 7.5 |
| 12.2 | 7.3 |
| 12.5 | 7.1 |
| 13.6 | 6.5 |
| 14.1 | 6.3 |
| 14.9 | 5.9 |
| 15.4 | 5.8 |
| 15.9 | 5.6 |
| 16.3 | 5.4 |
| 17.0 | 5.2 |
| 17.8 | 5.0 |
| 18.1 | 4.9 |
| 19.4 | 4.6 |
| 20.2 | 4.4 |
| 20.7 | 4.3 |
| 21.1 | 4.2 |
| 21.5 | 4.1 |
| 22.5 | 4.0 |
| 23.1 | 3.8 |
| 23.4 | 3.8 |
| 23.8 | 3.7 |
| 24.4 | 3.6 |
| 25.1 | 3.5 |
| 25.4 | 3.5 |
| 27.1 | 3.3 |

Example 2F 100 mg linaclotide was mixed with 0.1N hydrochloric acid containing a known amount of polymer (for example, polyvinyl pyrrolidone). The mixture was shaken using an end-over-end shaker for 6-48 hours at temperature in the range of 20° C. to 65° C. The suspension was carefully filtered into a glass container. A weighed amount of sodium chloride was added to the filtrate and it was stored at 4° C. After a suitable formation period, the α crystalline form of linaclotide was carefully isolated, washed, dried and analyzed using powder X-ray diffractometry. FIG. 10 shows the X-ray powder diffraction pattern for the crystalline form of linaclotide. Peak positions for the XRD are provided in Table 6.

TABLE 6

| 2-Theta (°) | d(Å) |
| --- | --- |
| 6.1 | 14.5 |
| 7.7 | 11.5 |
| 8.2 | 10.7 |
| 8.5 | 10.4 |
| 10.2 | 8.7 |
| 11.2 | 7.9 |
| 12.3 | 7.2 |
| 13.7 | 6.4 |
| 14.2 | 6.2 |
| 16.0 | 5.5 |
| 16.4 | 5.4 |
| 17.9 | 4.9 |
| 19.5 | 4.5 |
| 20.4 | 4.3 |
| 20.9 | 4.2 |
| 22.5 | 3.9 |
| 23.9 | 3.7 |
| 24.2 | 3.7 |
| 25.5 | 3.5 |
| 27.3 | 3.3 |
| 27.6 | 3.2 |

Example 2G 100 mg linaclotide was mixed with 0.1N nitric acid. The mixture was stirred using magnetic stirrer for 30-60 minutes at room temperature. The suspension was carefully filtered into a glass container and the filtrate was stored under room temperature conditions. After a suitable formation period, the α crystalline form of linaclotide was carefully isolated, washed, dried and analyzed using powder X-ray diffractometry. FIG. 11 shows the X-ray powder diffraction pattern for the crystalline form of linaclotide. Peak positions for the XRD are provided in Table 7.

TABLE 7

| 2-Theta (°) | d(Å) |
|---|---|
| 5.6 | 15.6 |
| 6.0 | 14.7 |
| 6.3 | 14.0 |
| 7.7 | 11.5 |
| 8.1 | 10.9 |
| 8.4 | 10.5 |
| 9.5 | 9.3 |
| 10.1 | 8.8 |
| 11.0 | 8.1 |
| 11.2 | 7.9 |
| 11.8 | 7.5 |
| 12.2 | 7.3 |
| 12.5 | 7.1 |
| 13.6 | 6.5 |
| 14.2 | 6.2 |
| 14.9 | 6.0 |
| 15.4 | 5.8 |
| 15.9 | 5.6 |
| 16.3 | 5.4 |
| 17.0 | 5.2 |
| 17.8 | 5.0 |
| 18.9 | 4.7 |
| 19.4 | 4.6 |
| 20.2 | 4.4 |
| 20.7 | 4.3 |
| 21.4 | 4.1 |
| 22.4 | 4.0 |
| 23.8 | 3.7 |
| 24.4 | 3.6 |
| 25.4 | 3.5 |

Example 2H 100 mg linaclotide was mixed with 0.1N methane sulfonic acid. The mixture was stirred using magnetic stirrer for 30-60 minutes at room temperature. The suspension was carefully filtered into a glass container and the filtrate was stored under room temperature conditions. After a suitable formation period, the α crystalline form of linaclotide was carefully isolated, washed, dried and analyzed using powder X-ray diffractometry. FIG. 12 shows the X-ray powder diffraction pattern for the crystalline form of linaclotide. Peak positions for the XRD are provided in Table 8.

TABLE 8

| 2-Theta (°) | d(Å) |
|---|---|
| 5.6 | 15.7 |
| 6.0 | 14.7 |
| 6.3 | 14.0 |
| 7.7 | 11.5 |
| 8.1 | 10.9 |
| 8.5 | 10.5 |
| 9.5 | 9.3 |
| 10.1 | 8.8 |
| 10.6 | 8.4 |
| 11.2 | 7.9 |
| 11.7 | 7.6 |
| 12.1 | 7.3 |
| 12.5 | 7.1 |
| 13.6 | 6.5 |
| 14.1 | 6.3 |
| 14.6 | 6.1 |
| 14.8 | 6.0 |
| 15.4 | 5.7 |
| 15.9 | 5.6 |
| 16.3 | 5.4 |
| 17.0 | 5.2 |
| 17.8 | 5.0 |
| 18.1 | 4.9 |
| 18.9 | 4.7 |
| 19.3 | 4.6 |
| 19.7 | 4.5 |
| 20.2 | 4.4 |
| 20.7 | 4.3 |
| 21.1 | 4.2 |
| 21.5 | 4.1 |
| 22.5 | 4.0 |
| 23.1 | 3.8 |
| 23.7 | 3.7 |
| 24.1 | 3.7 |
| 25.3 | 3.5 |

Example 2I 100 mg linaclotide was mixed with 0.1N hydrobromic acid. The mixture was stirred using magnetic stirrer for 30-60 minutes at room temperature. The suspension was carefully filtered into a glass container and the filtrate was stored under room conditions. After a suitable formation period, the α crystalline form of linaclotide was carefully isolated, washed, dried and analyzed using powder X-ray diffractometry. FIG. 13 shows the X-ray powder diffraction pattern for the crystalline form of linaclotide. Peak positions for the XRD are provided in Table 9.

TABLE 9

| 2-Theta (°) | d(Å) |
|---|---|
| 5.6 | 15.8 |
| 6.0 | 14.8 |
| 7.0 | 12.6 |
| 7.7 | 11.5 |
| 8.1 | 10.9 |
| 8.4 | 10.5 |
| 9.5 | 9.3 |
| 10.1 | 8.7 |
| 11.2 | 7.9 |
| 11.7 | 7.5 |
| 12.2 | 7.3 |
| 12.4 | 7.1 |
| 13.6 | 6.5 |
| 14.2 | 6.2 |
| 14.6 | 6.1 |
| 14.9 | 6.0 |
| 15.3 | 5.8 |
| 15.8 | 5.6 |
| 16.3 | 5.4 |
| 16.6 | 5.3 |
| 16.9 | 5.2 |
| 17.7 | 5.0 |
| 18.0 | 4.9 |
| 18.4 | 4.8 |
| 18.7 | 4.7 |
| 18.9 | 4.7 |
| 19.3 | 4.6 |

TABLE 9-continued

| 2-Theta (°) | d(Å) |
|---|---|
| 19.7 | 4.5 |
| 20.1 | 4.4 |
| 20.7 | 4.3 |
| 21.4 | 4.1 |
| 21.7 | 4.1 |
| 22.4 | 4.0 |
| 23.0 | 3.9 |
| 23.3 | 3.8 |
| 23.7 | 3.8 |
| 24.1 | 3.7 |
| 24.4 | 3.6 |
| 25.0 | 3.6 |
| 25.3 | 3.5 |

Example 3

Measurement of Linaclotide Content and Purity

The relative chemical purity and stability of amorphous and crystalline linaclotide was studied using reverse phase high performance liquid chromatography (HPLC). The chemical identification was conducted using reverse phase high performance liquid chromatography coupled with mass spectroscopy (HPLC-MS). The mass spectroscopic analysis was performed at Enhance MS scan (EMS) mode with positive ionization and a scan range (m/z) of 600-1600.

Methods
High Performance Liquid Chromatography (HPLC)

A Perkin Elmer series 200 LC instrument (Perkin Elmer, Waltham, Mass.) was used with a YMC Pro C18 column (150 mm×3.0 mm, 3 µm) (Waters Corporation, Milford, Mass.). The column temperature was set at 40° C. while the auto sampler temperature was maintained at 4° C. using a peltier tray. The injection volume was 50 µl. A gradient (0.6 ml/minute) run was used comprising of two solvents; A (97.9% Water, 2% Acetonitrile, 0.1% Trifluoroacetic Acid) and B (94.9% Acetonitrile, 5% Water, 0.1% Trifluoroacetic Acid). The gradient was set according to the scheme described in Table 10. The effluent was detected at 220 nm using a UV detector.

TABLE 10

Gradient scheme for HPLC method

| TIME (MINUTES) | % A | % B | COMMENTS |
|---|---|---|---|
| 0 | 100 | 0 | Initial Conditions |
| 4 | 100 | 0 | 4-minute hold |
| 9 | 90 | 10 | 5-minute linear gradient |
| 43 | 77 | 23 | 34-minute linear gradient |
| 49 | 66 | 34 | 6-minute linear gradient |
| 59 | 20 | 80 | 10-minute linear gradient |
| 60 | 100 | 0 | Return to initial conditions |
| 67 | 100 | 0 | Re-equilibration |

High Performance Liquid Chromatography-Mass Spectroscopy (HPLC-MS)

A Perkin Elmer Series 200 LC-MS instrument (Perkin Elmer, Waltham, Mass.) was used with a Pursuit XR C18 column (150×2 mm, 3 µm). The column temperature was set at 40° C. while the autosampler temperature was maintained at 4° C. using a peltier tray. The injection volume was 5 µl. A gradient (0.25 ml/minute) run was used comprising of two solvents; A (0.1% trifluoroacetic acid in water) and B (0.1% trifluoroacetic acid in acetonitrile). The gradient was set according to the scheme described in Table 11. The effluent was detected at 220 nm using a UV detector. The mass spectroscopic analysis was performed at Enhance MS scan (EMS) mode with positive ionization and a scan range (m/z) of 600-1600.

TABLE 11

Gradient scheme for HPLC-MS method

| TIME (MINUTES) | % A | % B | COMMENTS |
|---|---|---|---|
| 0 | 95 | 5 | Initial Conditions |
| 5 | 95 | 5 | 5-minute hold |
| 10 | 85 | 15 | 5-minute linear gradient |
| 40 | 75 | 25 | 30-minute linear gradient |
| 50 | 65 | 35 | 10-minute linear gradient |
| 60 | 25 | 75 | 10-minute linear gradient |
| 60.1 | 95 | 5 | Return to initial conditions |
| 70 | 95 | 5 | Re-equilibration |

Results

The precipitates prepared in Examples 1A and 2A were chemically identified as linaclotide based on HPLC-MS analysis. The purity of the precipitate was found to be in the range of 95% to 100%.

The solid-state chemical stability of the α-crystalline form of linaclotide was then compared to that of amorphous form linaclotide. Known quantities of test materials were placed in 45 cc high-density polyethylene bottles. The bottles were induction sealed and placed in 40° C./75% RH stability chamber. Two bottles were then withdrawn at the time points of 2 weeks, at 1 month, at 2 months, and at 3 months, and were analyzed after adequate dilution for assay. The normalized assay results are shown in Table 12.

TABLE 12

Solid-State chemical stability of amorphous and α-crystalline form of linaclotide

| | Amorphous Linaclotide | | α-Crystalline Linaclotide | |
|---|---|---|---|---|
| Time | Normalized Assay (Wt %) | Degradation Products (Wt %) | Normalized Assay (Wt %) | Degradation Products (Wt %) |
| Initial | 100.0 | 2.1 | 100.0 | 2.4 |
| 2 Weeks | 84.0 | 3.6 | 94.8 | 2.6 |
| 1 Month | 79.1 | 5.6 | 91.9 | 3.8 |
| 2 Months | 74.5 | 9.3 | 89.7 | 5.1 |
| 3 Months | 68.8 | 12.0 | 88.4 | 7.5 |

The remaining 19.2% and 4.1% of the amorphous and α-form linaclotide respectively may comprise multimers.

As is illustrated in Table 12, the α-crystalline form of linaclotide was found to have a substantially better stability profile than amorphous linaclotide, under the study conditions. Additionally, as is illustrated, the α-crystalline form of linaclotide had a significantly lower concentration of degradation products, as well as significantly less multimer formation.

As is illustrated in Table 13, the α-crystalline form of linaclotide was also found to have lower concentrations of degradation products (water mediated de-amidation and hydrolysis) and non-disulfide linked multimers as compared to amorphous linaclotide after storage for three months in induction sealed 45 cc high-density polyethylene bottles at 40° C./75% RH. On the other hand, acid-induced hydrolysis was pronounced in the crystalline form.

TABLE 13

Degradation Profile following 3 months storage in induction sealed 45 cc high-density polyethylene bottles under 40° C./75% RH

| | Degradation Products | | | |
|---|---|---|---|---|
| | Hydrolysis Product (Wt %) | Water-Mediated Products (Wt %) | Acetylation Product (Wt %) | Non-disulfide linked multimers (Wt %) |
| Amorphous linaclotide | 0.30 | 7.00 | 2.39 | 1.96 |
| Crystalline linaclotide | 5.70 | 0.40 | 0.31 | 0.07 |

Example 4

Isolation and Preparation of Linaclotide Hydrolysis Product

A linaclotide hydrolysis product was prepared by transforming Asn in the 7 position to Asp (the numbering of linaclotide starts with 1 at the N-terminal Cys). The linaclotide hydrolysis product was synthesized using a solid phase peptide synthesis technique. The structure of the linaclotide hydrolysis product is shown below (wherein the peptide sequence corresponds to SEQ ID NO 2):

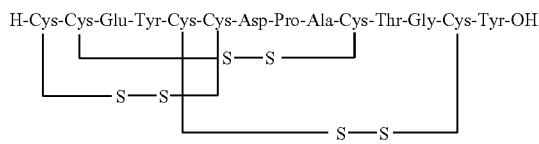

The linaclotide hydrolysis product may also be prepared by other methods known in the art, e.g., by isolation from linaclotide preparations using chromatographic techniques or by recombinant expression of a nucleic acid encoding the linaclotide hydrolysis product (CCEYCCDPACTGCY) (SEQ ID NO 2), optionally followed by oxidation of the cysteine residues to form the disulfide linkages.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure.

As is demonstrated in the Examples, and as is discussed in this application, the crystalline forms of linaclotide have physical properties (e.g., stability properties) that are surprising and unexpected as compared to amorphous linaclotide and/or other crystalline forms of linaclotide. The crystalline forms of linaclotide may also have synergy with other active or inactive components resulting in enhanced performance characteristics or properties of pharmaceutical compositions comprising one or more crystalline forms of the present invention.

The depicted and described embodiments of the invention are exemplary only, and are not exhaustive of the scope of the invention. Consequently, the invention is intended to be limited only by the spirit and scope of the appended claims, giving full cognizance to equivalence in all respects.

All references cited herein are hereby incorporated by reference in their entirety.

What is claimed is:

1. A crystalline form of linaclotide having an X-ray powder diffraction pattern comprising peaks at about 6.2, about 7.8, about 22.6 and about 23.9+/−0.5 degrees 2θ.

2. The crystalline form of claim 1, wherein the X-ray powder diffraction pattern further comprises a peak at about 19.5+/−0.5 degrees 2θ.

3. A pharmaceutical composition comprising the crystalline form of claim 1.

4. A process for preparing a crystalline form of linaclotide having an X-ray powder diffraction pattern comprising peaks at about 6.2, about 7.8, about 22.6 and about 23.9+/−0.5 degrees 2θ, comprising crystallizing linaclotide to form the crystalline form of linaclotide and optionally isolating the crystalline form of linaclotide.

5. The crystalline form of claim 1, wherein the crystalline form has a melting endotherm at about 270° C. as determined by DSC.

6. A crystalline form of linaclotide having a melting endotherm at about 270° C. as determined by DSC and X-ray powder diffraction pattern comprising characteristic peaks at about 7.8 and about 23.9+/−0.5 degrees 2θ.

* * * * *

```
SEQUENCE LISTING

<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 1

Cys Cys Glu Tyr Cys Cys Asn Pro Ala Cys Thr Gly Cys Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 2

Cys Cys Glu Tyr Cys Cys Asp Pro Ala Cys Thr Gly Cys Tyr
1               5                   10
```